US006673826B2

(12) United States Patent
Farber

(10) Patent No.: US 6,673,826 B2
(45) Date of Patent: *Jan. 6, 2004

(54) METHODS FOR TREATMENT OF INFLAMMATORY DISEASES

(75) Inventor: Elliott Farber, North Mankato, MN (US)

(73) Assignee: Alwyn Company, Inc., Lake Crystal, MN (US)

( * ) Notice: Subject to any disclaimer, the term of this patent is extended or adjusted under 35 U.S.C. 154(b) by 96 days.

This patent is subject to a terminal disclaimer.

(21) Appl. No.: 09/758,696

(22) Filed: Jan. 11, 2001

(65) Prior Publication Data

US 2001/0003753 A1 Jun. 14, 2001

Related U.S. Application Data

(63) Continuation-in-part of application No. 09/570,120, filed on May 12, 2000, which is a continuation-in-part of application No. 09/360,095, filed on Jul. 23, 1999.

(51) Int. Cl.[7] .................. A61K 31/415; A61K 9/13; A61K 9/107

(52) U.S. Cl. .................. 514/390; 514/390; 514/937; 514/938; 514/939; 514/940; 514/941; 514/943; 424/400; 424/401

(58) Field of Search .................. 514/390, 937, 514/939, 940, 941, 943, 938; 424/400, 401

(56) References Cited

U.S. PATENT DOCUMENTS

| | | |
|---|---|---|
| 3,830,824 A | 8/1974 | Margraf |
| 3,830,825 A | 8/1974 | Margraf |

(List continued on next page.)

FOREIGN PATENT DOCUMENTS

| | | | |
|---|---|---|---|
| EP | 0 030 157 A1 | 6/1981 | |
| EP | 0242553 | 10/1987 | .......... A61K/33/04 |

(List continued on next page.)

OTHER PUBLICATIONS

Kuroda et al, JP 58–140013, Translated copy.*
F.R. Greenbaum, "The Story of Allantoin," *Am. K. Pharm.* 112:205–216 (1940).
M.A. Lesser, Allantoin,: *Drug Cosmet. Ind.* 42:451–456, 469 (1938).

(List continued on next page.)

*Primary Examiner*—Russell Travers
*Assistant Examiner*—Shahnam Sharareh
(74) *Attorney, Agent, or Firm*—Hogan & Hartson LLP

(57) ABSTRACT

An improved method of treating skin diseases comprises applying to the skin of a patient suffering such a skin disease an allantoin-containing composition in a therapeutically effective quantity. The allantoin-containing composition is a water-in-oil emulsion that includes allantoin and an emulsifier system that includes at least one emulsifier that is either an anionic emulsifier or a nonionic emulsifier. If the emulsifier is an anionic emulsifier, the emulsifier system can include beeswax. The nonionic emulsifiers used can include at least one nonionic emulsifier that is an ethoxylated ether or an ethoxylated ester whose carbon chain length ranges from 8 to 22 carbon atoms. Alternatively, the emulsifier system can include an acidic anionic polymer such as carboxypolymethylene and an anionic emulsifier. In another alternative, the emulsifier system can include the acidic anionic polymer and a nonionic emulsifier, or the acidic anionic polymer alone. In still another alternative, the emulsifier system can include cetyl alcohol and stearic acid. In yet another alternative, the emulsifier system can include sodium stearoyl lactylate and sodium isostearoyl lactylate. In another alternative, the emulsifier system can include at least one polyethyleneglycol ether of cetearyl alcohol. In still another alternative, the emulsifier system can include a polyethylene glycol ester of stearic acid and glyceryl stearate. The composition can include other ingredients. The pH of the composition used in a method according to the present invention is from about 3.0 to about 6.0; preferably, a narrower pH range is used, varying with each embodiment of the composition. Among the diseases that can be treated is epidermolysis bullosa.

11 Claims, 12 Drawing Sheets

U.S. PATENT DOCUMENTS

| | | | |
|---|---|---|---|
| 3,830,908 A | 8/1974 | Klippel et al. | |
| 3,856,805 A | 12/1974 | Margraf | |
| 3,930,000 A | 12/1975 | Margraf | |
| 3,932,627 A | 1/1976 | Margraf | |
| 3,954,989 A | 5/1976 | Mecca | |
| 4,170,229 A | 10/1979 | Olson | |
| 4,184,978 A | 1/1980 | France et al. | 252/309 |
| 4,278,664 A | 7/1981 | Van Cleave | |
| 4,374,766 A | 2/1983 | Puchalski et al. | |
| 4,478,853 A | 10/1984 | Chaussee | |
| 4,507,279 A | 3/1985 | Okuyama et al. | |
| 4,670,263 A | 6/1987 | Noorlander | |
| 4,707,354 A | 11/1987 | Garlen et al. | |
| 4,708,813 A | 11/1987 | Snyder | |
| 4,767,618 A | 8/1988 | Grollier et al. | 424/74 |
| 4,806,262 A | 2/1989 | Snyder | |
| 4,822,601 A | 4/1989 | Goode et al. | 424/59 |
| 4,880,621 A | 11/1989 | Grollier et al. | |
| 4,933,177 A | 6/1990 | Grollier et al. | 424/74 |
| 4,981,845 A | 1/1991 | Pereira | |
| 5,112,886 A | 5/1992 | Phalangas | |
| 5,122,533 A | 6/1992 | Bar-On et al. | |
| 5,176,916 A | 1/1993 | Yamanaka et al. | 424/448 |
| 5,221,533 A | 6/1993 | Perlman | |
| 5,455,033 A | 10/1995 | Silverman et al. | |
| 5,476,664 A | 12/1995 | Robinson et al. | 424/443 |
| 5,512,200 A | 4/1996 | Garcia | |
| 5,567,427 A | 10/1996 | Papadakis | |
| 5,578,312 A | 11/1996 | Parrinello | |
| 5,616,347 A | 4/1997 | Alliger et al. | |
| 5,658,559 A | 8/1997 | Smith | |
| 5,661,170 A | 8/1997 | Chodosh | |
| 5,709,847 A | 1/1998 | Bissett et al. | |
| 5,736,128 A | 4/1998 | Chaudhuri et al. | |
| 5,753,245 A | 5/1998 | Fowler et al. | 424/401 |
| 5,824,666 A | 10/1998 | Deckner et al. | |
| 5,827,870 A | 10/1998 | Chodosh | |
| 5,830,483 A | 11/1998 | Seidel et al. | |
| 5,849,310 A | 12/1998 | Trinh et al. | |
| 5,863,548 A | 1/1999 | Elder | |
| 5,871,754 A | 2/1999 | Briggs et al. | |
| 5,871,762 A | 2/1999 | Venkitaraman et al. | 424/402 |
| 5,876,736 A | 3/1999 | Cohen et al. | |
| 5,885,581 A | 3/1999 | Massand | |
| 5,914,116 A | 6/1999 | Suares et al. | |
| 5,932,228 A | 8/1999 | Hall et al. | |
| 5,952,373 A | 9/1999 | Lanzendörfer et al. | |
| 5,958,436 A | 9/1999 | Hahn et al. | |
| 5,968,528 A | 10/1999 | Deckner et al. | |
| 6,001,377 A | 12/1999 | SaNogueira, Jr. et al. | |
| 6,060,061 A | 5/2000 | Breton et al. | |
| 6,077,520 A | 6/2000 | Tominaga | 424/401 |
| 6,080,393 A | 6/2000 | Liu et al. | |
| 6,086,903 A | 7/2000 | Trinh et al. | |
| 6,120,782 A | 9/2000 | Mansouri | |
| 6,169,114 B1 | 1/2001 | Yamaguchi et al. | 514/562 |
| 6,174,533 B1 | 1/2001 | SaNogueira, Jr. et al. | |
| 6,281,236 B1 | 8/2001 | Farber | 514/390 |
| 6,306,915 B1 | 10/2001 | Murata | |
| 6,329,413 B1 | 12/2001 | Farber | 514/390 |
| 6,337,065 B1 | 1/2002 | Jacobson et al. | |

FOREIGN PATENT DOCUMENTS

| | | | | |
|---|---|---|---|---|
| EP | 0380157 | 8/1990 | | A61K/33/04 |
| GB | 1346544 | 2/1974 | | C07D/49/32 |
| JP | 1-058165 A | 3/1989 | | |
| JP | 4-208219 A | 7/1992 | | |
| WO | WO 90/09779 | 9/1990 | | |
| WO | WO90/09779 | 9/1990 | | A61K/7/16 |

OTHER PUBLICATIONS

I.I. Lubowe & S.B. Mecca, "Allantoin and Aluminum Derivatives in Dermatological Applications," *Drug Cosmet. Ind.* 84:36, 37, 117 (1959).

S.B. Mecca, "Allantoin and the Newer Aluminum Allantoinates," *Proc. Scient. Sect. Toilet Goods Assoc.* No. 31:1–6 (1959).

S.B. Mecca, "The Function and Applicability of the Allantoinates," *Proc. Scient. Sect. Toilet Goods Assoc.* No. 39:7–15 (1963).

P. LeVan et al., "The Use of Silicones in Dermatology," *Calif. Med.* 8:210–213 (1954).

R. Cahen & A. Pessonnier, "Etude Pharmacologique de L'Allantoïnate de Dihydroxyaluminium et de L'Allantoïnate de Chlorhydroxy–aluminium. I.—Toxicité," *Ann. Pharm. Franç.* 20:623–636 (1962) (in French), discloses the physical and chemical properties and the toxicity of dihydroxyaluminum allantoinate and chlorhydroxyaluminum allantoinate. The compounds were observed to have no toxicity.

R. Cahen & J.–F. Clement, "Etude Pharmacologique de L'Allantoïnate de Dihydroxyaluminium et de L'Allantoïnate de Chlorhydroxy–aluminium. II.—Etude de l'Activité Gastrique," *Ann. Pharm. Franç.* 20:693–703 (1962) (in French), discloses the activity of dihydroxyaluminum allantoinate and chlorhydroxyaluminum allantoinate on gastric activity. The compounds were found to have acid–neutralizing and buffering activity and to diminish gastric acidity.

R. Cahen & A. Pessonnier, "Etude Pharmacologiqie de L'Allantoïnate de Dihydroxyaluminium et de L'Allantoïnate de Chlorhydroxyaluminium. III.—Effet Anti–ulcéreux," *Ann. Pharm. Franç.* 20:704–713 (1962) (in French), discloses the anti–ulcer activity of the compounds dihydroxyaluminum allantoinate and chlorhydroxyaluminum allantoinate. The compounds were found to have anti–ulcer activity in rats and guinea pigs comparable to compounds such as aluminum hydrate and bismuch subnitrate.

R. Cahen & A. Pessonnier, "Etude Pharmacologique de L'Allantoënate de Dihydroxyaluminium et de L'Allantoïnate de Chlorhydroxyaluminium. IV.—Effet sur l'Ulcère Médicamenteux Expérimental," *Ann. Pharm. Franç.* 21:215–222 (1963) (in French), discloses the effect of the compounds dihydroxyaluminum allantoinate and chlorhydroxyaluminum allantoinate on ulcers produced in the rat administration of phenylbutazone or reserpine. The compounds were found to have activity against such ulcers.

C. Debray et al., "Etude de Dèrivés Allantoïniques de l'Aluminium dans la Thérapeutique des Affections Gastro–duodénales," *Presse Méd.* 70:2643 (1962) (in French) discloses the activity of the compounds dihydroxyaluminum allantoinate and chlorhydroxyaluminum allantoinate administered in a complex with a polymer of polyoxyethylene and polyoxypropanediol, methlhomatropine bromide, and calcium carbonate on gastrointestinal conditions. The complex was said to be effective against duodenal ulcer and effective in protecting the gastric mucosa.

Japanese patent publication No. JP 58140013 A Daiichi Seiyaku Co., published Aug. 19, 1983.

Publication—product information insert for Alphosyl Cream and Alphosyl Lotion, G.D. Searle (South Africa), Apr. 24, 1975.

Publication—product information insert for Clearasil Medicated Facial Cleanser, Procter & Gamble (South Africa) Jan. 31, 1994.

Publication—product information insert fo Arola Rosebaum, Supramed Limited, Jan. 12, 1986.

Abstract of a publication—M.Cajkovac et al., "Influence of Emulsoid Vehicle on the Release and Activity of Allantoin," *Pharmazie* 47: 39–43 (1992) (abstract only).

Abstract of a publication—M. Maragakis et al., "Possibilities of Scar Treatment After Thoracic Surgery," *Drugs Under Exp. & Clin. Res.* 21: P199–206 (1995) (abstract only).

Publication—product information insert for Alphosyl, undated.

Abstract of a publication—G. Stinco et al., "Seborrheic Dermatitis Treated with Furalglucitole Cream," *Dermatol. Clin.* 18: 78–81 (1998) (abstract only).

Abstract of a publication—M. Maragakis et al., "Possibilities of Scar Treatment After Thoracic Surgery," *Drugs Exp. Clin. Res.* 21: P:199–206 (1999) (abstract only).

Abstract of publication—G.H. Willital & H. Heine, "Efficiency of Contractubex® Gel in the Treatment of Fresh Scars After Thoracic Surgery in Children and Adolescents," *Int. J. Clin. Pharmacol. Res.* 14: 193–202 (1994) (abstract only).

Publication, H.W. Margraf & T.H. Covey, Jr., "A Trial of Silver–Zinc–Allantoinate in the Treatment of Leg Ulcers," *Arch. Surg.* 12: 699–704 (1977).

Publication, Remington: The Science and Practice of Pharmacy (19$^{th}$ Ed. 1995, Mack Publishing Co., Easton, Penn.), p. 640.

Publication, D. Hoffmann, "The Complete Illustrated Herbal," (Barnes and Nobles, 1996), pp. 63, 104.

* cited by examiner

METHODS FOR TREATMENT OF INFLAMMATORY DISEASES

CROSS-REFERENCES

This application is a continuation-in-part application of application Ser. No. 09/570,120, entitled "Methods for Treatment of Inflammatory Diseases," filed May 12, 2000 by Elliott Farber, which in turn is a continuation-in-part application of application Ser. No. 09/360,095, entitled "Oil-in-Water Emulsion With Improved Stability," filed Jul. 23, 1999 by Elliott Farber. Both of these prior applications are hereby incorporated in their entirety by this reference.

BACKGROUND OF THE INVENTION

The present invention is directed to improved methods of treating inflammatory skin disease.

Inflammatory skin disease, particularly chronic inflammatory skin disease, is still a major source of morbidity. Such inflammatory skin diseases are disfiguring and cause severe physical and psychological harm to patients, disrupting their quality of life substantially. Such diseases include decubitus ulcers, pressure ulcers, diabetic ulcers, epidermolysis bullosa, and milia. Such skin diseases tend to be chronic and difficult to treat, particularly in patients with poor circulation or other underlying disease states.

Among the most difficult of these diseases to treat is epidermolysis bullosa. Epidermolysis bullosa occurs in newborns and infants and causes severe inflammation, blistering, and scarring.

Accordingly, there is a need for an improved method of treating these inflammatory skin diseases. Such a method should be effective in a wide variety of skin diseases, and should be suitable for use together with other treatment modalities. It should be well tolerated by the patients without side effects. This is particularly important because many of these diseases have an underlying allergic component that makes their treatment difficult and may prevent the use of a number of previously known agents.

SUMMARY

An improved method of treating such skin diseases comprises applying to the skin of a patient suffering such a skin disease an allantoin-containing composition in a therapeutically effective quantity.

The allantoin-containing composition comprises an oil-in-water emulsion including at least one emulsifier and can contain other ingredients, such as a chelating agent to bind metal ions that might accelerate degradation of the composition. A particularly preferred chelating agent is EDTA. The EDTA can be added in various acid or salt forms depending on the pH of the composition, such as EDTA itself, disodium EDTA, or tetrasodium EDTA.

In one embodiment of the invention, the allantoin-containing composition comprises an oil-in-water emulsion comprising:

(1) allantoin;
(2) an emulsifier system including:
  (a) beeswax; and
  (b) an anionic emulsifier that is substantially hydrophilic and is soluble in water, the pH of the composition being from about 3.0 to about 6.0 after the addition of acid to bring the pH to a value within the range of from about 3.0 to about 6.0. Preferably, the pH of the composition is from about 4.5 to about 5.8.

The emulsifier can be selected from the group consisting of ammonium lauryl sulfate, sodium lauryl sulfate, sodium laureth sulfate, sodium oleyl succinate, ammonium lauryl sulfosuccinate, sodium dodecylbenzenesulfonate, ammonium laureth sulfate, and sodium lauryl sarcosinate. Preferably, the emulsifier is sodium lauryl sulfate.

In another embodiment, the allantoin-containing composition comprises an oil-in-water emulsion comprising:

(1) allantoin;
(2) an emollient component comprising:
  (a) lanolin oil;
  (b) cetyl alcohol;
  (c) stearyl alcohol; and
  (d) cod liver oil;
(3) butylated hydroxytoluene;
(4) an emulsifier system comprising at least one nonionic emulsifier that is an ethoxylated ether or an ethoxylated ester whose carbon chain length ranges from 8 to 22 carbon atoms; and
(5) at least one acid selected from the group consisting of:
  (a) an organic acid of from 2 to 22 carbon atoms; and
  (b) an inorganic acid selected from the group consisting of hydrochloric acid, sulfuric acid, and phosphoric acid to adjust the pH from about 3.0 to about 6.0. Preferably, the pH of the composition is from about 4.5 to about 5.8.

In yet another embodiment, the allantoin-containing composition comprises an oil-in-water emulsion comprising:

(1) allantoin;
(2) an emulsifier system including at least one nonionic emulsifier that is an ethoxylated ether or an ethoxylated ester whose carbon chain length ranges from 8 to 22 carbon atoms, the pH of the emulsion being from about 3.0 to about 6.0 after the addition of acid to bring the pH to a value within the range of from about 3.0 to about 6.0. Preferably, the pH of the composition is from about 4.5 to about 5.8.

In still another embodiment, the allantoin-containing composition comprises an oil-in-water emulsion comprising:

(1) allantoin; and
(2) an emulsifier system comprising:
  (a) an acidic anionic polymer; and
  (b) a polyethylene glycol ester of stearic acid.

The pH of the composition is adjusted to a value within a range of from about 3.0 to about 6.0. Preferably, the pH of the composition is from about 5.0 to about 6.0.

The composition can further comprise a carbohydrate polymer selected from the group consisting of galactoarabinan, polygalactose, and polyarabinose; preferably, the carbohydrate polymer is galactoarabinan.

In yet another alternative embodiment, the allantoin-containing composition comprises an oil-in-water emulsion comprising:

(1) allantoin; and
(2) an emulsifier system comprising:
  (a) an acidic anionic polymer; and
  (b) an anionic emulsifier that is substantially hydrophilic and is soluble in water.

The pH of the composition is adjusted to a value in a range from about 3.0 to about 6.0. Preferably, the pH of the composition is from about 5.0 to about 6.0.

The anionic emulsifier can be selected from the group consisting of sodium lauryl sulfate, sodium laureth sulfate, sodium oleyl succinate, sodium dodecylbenzenesulfonate and sodium lauryl sarcosinate. Preferably, the anionic emulsifier is sodium lauryl sulfate.

Typically, the acidic anionic polymer is carboxypolymethylene.

Preferably, in this embodiment, the composition further comprises a carbohydrate polymer selected from the group consisting of galactoarabinan, polygalactose, and polyarabinose. More preferably, the carbohydrate polymer is galactoarabinan.

In yet another alternative, the allantoin-containing composition comprises an oil-in-water emulsion comprising:

(1) allantoin; and
(2) an emulsifier system comprising:
   (a) an acidic anionic polymer; and
   (b) a nonionic emulsifier that is an ethoxylated ether or an ethoxylated ester whose carbon chain length ranges from 8 to 22 carbon atoms, wherein the pH of the composition is from about 3.0 to about 6.0. Preferably, the pH of the composition is from about 5.0 to about 6.0.

The acidic anionic polymer is preferably carboxypolymethylene as described above.

Preferably, in this embodiment as well, the composition further comprises a carbohydrate polymer selected from the group consisting of galactoarabinan, polygalactose and polyarabinose. More preferably, the carbohydrate polymer is galactoarabinan.

In this embodiment, the emulsifier system can further comprise glyceryl stearate.

In yet another embodiment of a method according to the present invention, the ethyoxylated ether or ethoxylated ester is omitted in the composition. In this embodiment, the composition comprises an oil-in-water emulsion comprising:

(1) allantoin;
(2) an emulsifier system comprising an acidic anionic polymer;
(3) an organic or inorganic base to adjust the pH to a value in a range of from about 3.0 to about 6.0. Preferably, the pH of the composition is from about 5.0 to about 5.5.

Preferably, the base is triethanolamine, and the acidic anionic polymer is a carboxypolymethylene polymer as described above.

Yet another embodiment of a method according to the present invention uses an allantoin-containing composition comprising an oil-in-water emulsion comprising:

(1) allantoin;
(2) an emulsifier system comprising:
   (a) cetyl alcohol; and
   (b) stearic acid; and
(3) a weak organic base to adjust the pH to a value within a range of from about 3.0 to about 6.0. Preferably, the pH of the composition is from about 5.0 to about 5.8.

Typically, the weak organic base is triethanolamine.

Still another embodiment of a method according to the present invention uses an allantoin-containing composition comprising an oil-in-water emulsion comprising:

(1) allantoin; and
(2) an emulsifier system comprising:
   (a) sodium stearoyl lactylate;
   (b) sodium isostearoyl lactylate;
   (c) optionally, triethanolamine stearate; and
   (d) optionally, at least one nonionic emulsifier selected from the group consisting of a nonionic emulsifier that is an ethoxylated ether or an ethoxylated ester whose carbon chain length ranges from 8 to 22 carbon atoms; and
(3) an acid to adjust the pH to a value within a range of from about 3.0 to about 6.0. Preferably, the pH of the composition is from about 5.0 to about 5.8.

Typically, the acid is citric acid.

Still another embodiment of a method according to the present invention uses an allantoin-containing composition comprising an oil-in-water emulsion comprising:

(1) allantoin; and
(2) an emulsifier system comprising at least one polyethyleneglycol ether of cetearyl alcohol; and
(3) an acid to adjust the pH of the composition to a value within a range of from about 3.0 to about 6.0. Preferably, the pH of the composition is from about 5.0 to about 5.8.

Typically, the acid is citric acid.

In polyethylene glycol ethers of cetearyl alcohol suitable for use in compositions in this embodiment of a method according to the present invention, the number of ethylene glycol moieties can range from 6 to 40, e.g., $R(OCH_2CH_2)_{25}OH$ where $R=CH_3(CH_2)_{16-18}$. In one preferred composition suitable for use in this embodiment of a method according to the present invention, the emulsifier system comprises both ceteareth-25 and ceteareth-6, i.e., polyethylene glycol ethers of cetearyl alcohol with 25 and 6 ethylene glycol units respectively.

Yet another embodiment of a method according to the present invention uses an allantoin-containing composition comprising an oil-in-water emulsion comprising:

(1) allantoin; and
(2) an emulsifier system comprising:
   (a) a polyethylene glycol ester of stearic acid; and
   (b) glyceryl stearate; and
(3) an acid to adjust the pH of the composition to a value within a range of from about 3.0 to about 6.0. Preferably, the pH of the composition is from about 5.0 to about 5.8.

Typically, the number of ethylene glycol moieties in the polyethylene glycol ester of stearic acid is from 25 to 100. Two preferred polyethylene glycol esters of stearic acid for use in compositions for an embodiment of a method according to the present invention are PEG-40 stearate and PEG-100 stearate, with 40 and 100 ethylene glycol moieties respectively. A particularly preferred polyethylene glycol ester of stearic acid is PEG-100 stearate.

Typically, the acid is citric acid.

In yet another alternative embodiment, the allantoin-containing composition comprises an oil-in-water emulsion comprising:

(1) allantoin;
(2) a carbohydrate polymer; and
(3) an emulsifier system comprising:
   (a) beeswax; and
   (b) an anionic emulsifier that is substantially hydrophilic and is soluble in water.

The pH of the composition is between about 3.0 and about 6.0. Preferably, the pH of the composition is from about 5.0 to about 6.0.

In all of these alternative embodiments, the composition can further comprise additional ingredients if they are not already included.

For example, the composition can further comprise an emollient component. The emollient component can comprise at least one emollient selected from the group consisting of lanolin oil, cetyl alcohol, stearyl alcohol, and cod liver oil.

The composition can further comprise an antioxidant such as butylated hydroxytoluene.

The composition can further comprise a preservative component. The preservative component can comprise at least one preservative selected from the group consisting of methylparaben and propylparaben.

The composition can further comprise a chelating agent. A preferred chelating agent is tetrasodium EDTA.

The composition can further comprise a solvent component. The solvent component can comprise at least one solvent selected from the group consisting of propylene glycol, butylene glycol, and glycerin. Preferably, the solvent component is propylene glycol.

The composition can further comprise a preservative component. The preservative component can comprise at least one preservative selected from the group consisting of methylparaben, propylparaben, and diazolidinyl urea.

The skin condition or disease to be treated can be one of epidermolysis bullosa, decubitus ulcers, pressure ulcers, diabetic ulcers, and milia. An important skin condition or disease that is treated by methods according to the present invention is epidermolysis bullosa.

Methods according to the present invention can further comprise administering an additional therapeutic agent in a therapeutically effective quantity. The additional therapeutic agent can be selected from the group consisting of steroids, nonsteroidal anti-inflammatory agents, leukotriene antagonists, and monoclonal antibodies.

BRIEF DESCRIPTION OF THE DRAWINGS

These and other features, aspects, and advantages of the present invention will become better understood with reference to the following description, appended claims, and accompanying drawings where:

DESCRIPTION

Figure 1A:
FIGS. 1(a) and 1(b) are pictures of the right foot of a first patient (A.B.) before the use of the cream of Example 2 from two different views, showing the severity of the disease.

I have unexpectedly found that a stabilized oil-in-water emulsion containing allantoin plus other ingredients provides a high degree of relief for inflammatory skin conditions characterized by ulceration, inflammation, or blistering of the skin.

In general, a method of treating such a skin condition or disease comprises applying to the skin an allantoin-containing composition in a therapeutically effective amount. The allantoin-containing composition comprises an oil-in-water emulsion as described below.

The allantoin-containing composition comprises an oil-in-water emulsion including at least one emulsifier and can contain other ingredients, such as a chelating agent to bind metal ions that might accelerate degradation of the composition. A particularly preferred chelating agent is EDTA. The EDTA can be added in various acid or salt forms depending on the pH of the composition, such as EDTA itself, disodium EDTA, or tetrasodium EDTA.

The skin condition or disease to be treated can be decubitus ulcers, pressure ulcers, diabetic ulcers, or milia. As described below in Examples 10–11, methods of the present invention are particularly suited for the treatment of epidermolysis bullosa.

In one embodiment of the present invention, the allantoin-containing composition comprises an oil-in-water emulsion comprising:

(1) allantoin; and
(2) an emulsifier system including:
  (i) beeswax; and
  (ii) an anionic emulsifier that is substantially hydrophilic and is soluble in water.

The pH of the emulsion is from about 3.0 to about 6.0 after the addition of acid to bring the pH into this range. Preferably, the pH of the emulsion is from about 4.5 to about 5.8.

The anionic emulsifier is typically one of ammonium lauryl sulfate, sodium laureth sulfate, sodium oleyl succinate, ammonium lauryl sulfosuccinate, sodium dodecylbenzenesulfonate, ammonium laureth sulfate, sodium N-lauryl sarcosinate, or sodium lauryl sulfate. A particularly preferred anionic emulsifier is sodium lauryl sulfate.

The composition further includes an acid to reduce the pH to a value within a range from about 3.0 to about 6.0, preferably a range from about 4.5 to about 5.8. The acid can be an organic acid, an inorganic acid, or a mixture of both.

Preferred organic acids include organic acids whose carbon chain length ranges from 2 to 22 carbon atoms and can be monocarboxylic, dicarboxylic, or tricarboxylic acids. The acids can be aliphatic or aromatic. Particularly preferred organic acids include citric acid, ascorbic acid, glycolic acid, benzoic acid, and salicylic acid. A most particularly preferred organic acid is citric acid.

Typically, the inorganic acid is a strong acid. It can be a monoprotic, diprotic, or triprotic acid. Particularly preferred inorganic acids include hydrochloric acid, sulfuric acid, or phosphoric acid.

For the embodiments described above, the composition can further include other ingredients. For example, the composition can include an emollient component for smoothness. The emollient component can include at least one of lanolin oil, cetyl alcohol, stearyl alcohol, and cod liver oil. Preferably, the emollient component comprises all of lanolin oil, cetyl alcohol, stearyl alcohol, and cod liver oil.

The composition can also include an antioxidant to prevent rancidity of ingredients such as cod liver oil. A preferred antioxidant is butylated hydroxytoluene (BHT).

The composition can further include a solvent component. Typically, the solvent component is one or more of propylene glycol, butylene glycol, and glycerin. Preferably, the solvent component is propylene glycol.

The composition can further include a chelating agent to bind metal ions that might acceleration degradation of the composition. A particularly preferred chelating agent is tetrasodium EDTA.

The composition can further include herbal extracts. The herbal extracts can include one or more of St. John's wort extract, witch hazel extract, chamomile extract, and arnica extract. The composition can include all of St. John's wort extract, witch hazel extract, chamomile extract, and arnica extract. However, typically, in compositions used in methods according to the present invention, herbal extracts are omitted.

The composition can further include a preservative such as at least one of methylparaben, ethylparaben, propylparaben, butylparaben, or phenoxyethanol. Preferably, the composition comprises methlylparaben and propylparaben as preservatives.

The composition can further include fragrance. The use of fragrance is well known in the art of over-the-counter drug formulation, and many suitable fragrances are known in the art. The stability and function of the composition is not altered by the presence or absence of fragrance. In many alternatives, it may be desirable to avoid the use of fragrance which may trigger allergic reactions in patients predisposed to such reactions.

The composition can further include other ingredients, such as proteins, humectants, other preservatives, essential oils, other vitamins, colorants, hydroxyacids, other plant extracts, sunscreens, sodium hyaluronate, lipids, fatty acids, thickeners, panthenol, and the like. The use of such components is conventional in the over-the-counter drug art. Typical sunscreens are octyl methoxycinnamate and benzophenone-3.

The following discussion describes ranges, preferred concentrations, and optimum concentrations for preferred compositions when the pH of the composition is from about 4.5 to about 5.8 useful in this embodiment of methods according to the present invention.

Water can comprise from about 50.0% to about 90.0% of the composition. Preferably, water comprises from about 55.0% to about 75.0% of the composition. An optimum concentration of water is about 68.68%.

Sodium lauryl sulfate, as a 30% solution, can comprise from about 0.5% to about 2.5% of the composition. Preferably, sodium lauryl sulfate comprises from about 1.0% to about 2.5% of the composition. An optimum concentration of sodium lauryl sulfate in the composition is about 1.90%.

Propylene glycol can comprise from about 2.0% to about 9.0% of the composition. Preferably, propylene glycol comprises from about 3.0% to about 6.0% of the composition. An optimum concentration of propylene glycol is about 5.30% of the composition.

Tetrasodium EDTA can comprise from about 0.05% to about 0.50% of the composition. Preferably, tetrasodium EDTA comprises from about 0.1% to about 0.30% of the composition. An optimum concentration of tetrasodium EDTA is about 0.15% of the composition.

Citric acid can comprise from about 0.05% to about 0.50% of the composition. A preferred concentration of citric acid is from about 0.08% to about 0.35% of the composition. An optimum concentration of citric acid is about 0.12% of the composition.

Lanolin oil can comprise from about 5.0% to about 15.0% of the composition. Preferably, lanolin oil comprises from about 8.0% to about 12.0% of the composition. An optimum concentration of lanolin oil is about 10.60% of the composition.

Cetyl alcohol can comprise from about 3.0% to about 10.0% of the composition. A preferred concentration of cetyl alcohol is from about 3.5% to about 7.5% of the composition. An optimum concentration of cetyl alcohol is about 4.20% of the composition.

Stearyl alcohol can comprise from about 1.0% to about 5.0% of the composition. A preferred concentration of stearyl alcohol is from about 1.0% to about 3.0% of the composition. An optimum concentration of stearyl alcohol is about 2.00% of the composition.

Beeswax can comprise from about 0.5% to about 2.5% of the composition. A preferred concentration of beeswax is from about 1.0% to about 2.5% of the composition. An optimum concentration of beeswax is about 1.90% of the composition.

Cod liver oil can comprise from about 1.0% to about 7.0% of the composition. Preferably, cod liver oil comprises from about 1.0% to about 4.0% of the composition. An optimum concentration of cod liver oil is about 2.00% of the composition.

Butylated hydroxytoluene can comprise from about 0.1% to about 1.0% of the composition. Preferably, butylated hydroxytoluene comprises from about 0.2% to about 0.8% of the composition. An optimum concentration of butylated hydroxytoluene is about 0.50% of the composition.

St. John's wort extract can comprise from about 0.05% to about 0.5% of the composition. Preferably, St. John's wort extract comprises from about 0.05% to about 0.15% of the composition. An optimum concentration of St. John's wort extract is about 0.10% of the composition.

Witch hazel extract can comprise from about 0.05% to about 0.5% of the composition. Preferably, witch hazel extract comprises from about 0.05% to about 0.15% of the composition. An optimum concentration of witch hazel extract is about 0.10% of the composition.

Chamomile extract can comprise from about 0.05% to about 0.50% of the composition. A preferred concentration of chamomile extract is from about 0.05% to about 0.15% of the composition. An optimum concentration of chamomile extract is about 0.10% of the composition.

Arnica extract can comprise from about 0.05% to about 0.50% of the composition. Preferably, arnica extract comprises from about 0.05% to about 0.15% of the composition. An optimum concentration of arnica extract is about 0.10% of the composition.

Methylparaben can comprise from about 0.10% to about 0.50% of the composition. A preferred concentration of methylparaben is from about 0.15% to about 0.40% of the composition. An optimum concentration of methylparaben is about 0.30% of the composition.

Propylparaben can comprise from about 0.10% to about 0.50% of the composition. A preferred concentration of propylparaben is from about 0.10% to about 0.30% of the composition. An optimum concentration of propylparaben is about 0.25% of the composition.

Allantoin can comprise from about 0.50% to about 2.0% of the composition. A preferred concentration of allantoin is from about 0.50% to about 2.0% of the composition. An optimum concentration of allantoin is about 1.50% of the composition.

If present, fragrance can comprise from about 0.05% to about 0.50% of the composition. Preferably, fragrance comprises from about 0.10% to about 0.30% of the composition. If present, an optimum concentration of fragrance is about 0.20% of the composition. As indicated above, in many embodiments it is desirable to omit fragrance to avoid the possibility of allergic reactions.

In another embodiment, the composition comprises an oil-in-water emulsion comprising:

(1) allantoin; and
(2) an emulsifier system including at least one nonionic emulsifier that is an ethoxylated ether or an ethoxylated ester whose carbon chain length ranges from 8 to 22 carbon atoms. As described above, the pH of the composition is from about 3.0 to about 6.0 after addition of acid. Preferably, the pH of the composition is from about 4.5 to about 5.8.

The composition used in this embodiment of the method can further include other ingredients as described above. For example, the composition can further include:

(1) an emollient component comprising at least one emollient selected from the group consisting of lanolin oil, cetyl alcohol, stearyl alcohol, and cod liver oil;
(2) butylated hydroxytoluene;
(3) at least one herbal extract selected from the group consisting of St. John's wort extract, witch hazel extract, chamomile extract, and arnica extract;
(4) a preservative component comprising at least one preservative selected from the group consisting of methylparaben, propylparaben, and diazolidinyl urea;
(5) tetrasodium EDTA; and
(6) a solvent component comprising at least one solvent selected from the group consisting of propylene glycol, butylene glycol, and glycerin.

In yet another embodiment of a method according to the present invention, the composition comprises an oil-in-water emulsion comprising:

(1) allantoin;
(2) an emollient component comprising:
   (a) lanolin oil;
   (b) cetyl alcohol;
   (c) stearyl alcohol; and
   (d) cod liver oil;
(3) butylated hydroxytoluene;
(4) an emulsifier system comprising at least one nonionic emulsifier that is an ethoxylated ether or an ethoxylated ester whose carbon chain length ranges from 8 to 22 carbon atoms; and
(5) at least one acid selected from the group consisting of:
   (a) an organic acid of from 2 to 22 carbon atoms; and
   (b) an inorganic acid selected from the group consisting of hydrochloric acid, sulfuric acid, and phosphoric acid to adjust the pH from about 3.0 to about 6.0. Preferably, the pH of the composition is from about 4.5 to about 5.8

The composition can further include other ingredients as described above. For example, the composition can further include:

(1) at least one herbal extract selected from the group consisting of St. John's wort extract, witch hazel extract, chamomile extract, and arnica extract;
(2) a preservative component comprising at least one preservative selected from the group consisting of methylparaben, propylparaben, and diazolidinyl urea;
(3) tetrasodium EDTA; and
(4) a solvent component comprising at least one solvent selected from the group consisting of propylene glycol, butylene glycol, and glycerin.

In still another embodiment of the method, the allantoin-containing composition comprises an oil-in-water emulsion comprising:

(1) allantoin; and
(2) an emulsifier system comprising:
   (a) an acidic anionic polymer; and
   (b) a polyethylene glycol ester of stearic acid.

The pH of the composition is adjusted to a value in the range of from about 3.0 to about 6.0. Preferably, the pH of the composition is from about 5.0 to about 6.0. The pH is adjusted with sodium hydroxide or other base as required.

The acidic anionic polymer is preferably a carboxypolymethylene polymer. Such polymers are marketed under the brand names "Carbomer" and "Carbopol." A suitable carboxypolymethylene polymer is marketed by B.F. Goodrich under the brand name "Carbomer." This is a slightly cross-linked polyacrylic acid that is from 1% to 2% cross-linked by allylsucrose or allylpentaerythritol with the polyacrylic acid. The resulting molecular weight range of this polymer is from about $2 \times 10^6$ daltons to about $1 \times 10^9$ daltons. The average molecular weight of this polymer is about $4 \times 10^6$ daltons.

Preferably, the concentration of the carboxypolymethylene polymer is from about 0.5% to about 2% of the composition.

The composition can further comprise a carbohydrate polymer. Typically, the carbohydrate polymer is selected from the group consisting of galactoarabinan, polygalactose, and polyarabinose. Preferably, the carbohydrate polymer is galactoarabinan. Galactoarabinan is derived from trees of the genus Larix (larch) and is a hemicellulosic product easily extractable by water in a pure form. The molecular weight of the galactoarabinan is about 20,000. Galactoarabinan has been consumed by humans in common foods such as carrots, tomatoes, maple syrup, soybeans, and wheat flour, among others. A suitable source of galactoarabinan is Larex, Inc (White Bear Lake, Minn.). Typically, the composition contains from about 1% to about 25% of galactoarabinan. Preferably, the composition contains from about 2% to about 10% of the carbohydrate polymer.

The composition used in this embodiment of a method according to the present invention can further include other ingredients. For example, the composition can include an emollient component for smoothness. The emollient component can include at least one emollient selected from the group consisting of lanolin oil, cetyl alcohol, stearyl alcohol, and cod liver oil.

The composition can also include an antioxidant to prevent rancidity of ingredients such as cod liver oil. A preferred antioxidant is butylated hydroxytoluene (BHT).

The composition can further include a solvent component. Typically, the solvent component can include at least one solvent selected from the group consisting of propylene glycol, glycerin, and butylene glycol. Preferably, the solvent component is propylene glycol.

The composition can further include a preservative component. The preservative component can include at least one preservative selected from the group consisting of methylparaben, propylparaben, and diazolidinyl urea. Preferably, the preservative component comprises methylparaben, propylparaben, and diazolidinyl urea.

The composition can further include fragrance. The use of fragrance is well known in the cosmetic art and in the art of over-the-counter drug formulation, and many suitable fragrances are known in the art. The stability and function of the cream is not altered by the presence or absence of fragrance.

Optionally, the composition can further include herbal extracts. The herbal extracts can include one or more of St. John's wort extract, witch hazel extract, chamomile extract, and arnica extract. However, these herbal extracts are typically omitted in the composition used in this embodiment of a method according to the present invention.

The composition can optionally further include other components, such as proteins, humectants, other preservatives, essential oils, other vitamins, colorants, hydroxyacids, other plant extracts, chelators, sunscreens, sodium hyaluronate, lipids, fatty acids, thickeners, panthenol, and the like. The use of such components is conventional in the cosmetic art and in the over-the-counter drug art. Typical sunscreens are octyl methoxycinnamate and benzophenone-3.

The following discussion describes ranges, preferred concentrations and optimum concentrations for preferred compositions useful in this embodiment of the present invention when the pH of the composition is from about 5.0 to about 6.0.

Water can comprise from about 50.0% to about 90.0% of the composition. Preferably, water comprises from about 60.0% to about 85.0% of the composition. An optimum concentration of water in the composition is about 69.95%.

The carboxypolymethylene polymer can comprise from about 0.30% to about 3.0% of the composition. Preferably, the carboxypolymethylene polymer comprises from about 0.50% to about 2.0% of the composition. An optimum concentration of the carboxypolymethylene polymer is about 0.85% of the composition.

Propylene glycol can comprise from about 2.0% to about 9.0% of the composition. Preferably, propylene glycol comprises from about 4.0% to about 7.0% of the composition. An optimum concentration of propylene glycol is about 5.70% of the composition.

PEG-100 stearate can comprise from about 0.25% to about 2.5% of the composition. Preferably, PEG-100 stearate comprises from about 0.50% to about 2.0% of the composition. An optimum concentration of PEG-100 stearate is about 1.50% of the composition.

Lanolin oil can comprise from about 5.0% to about 15.0% of the composition. Preferably, lanolin oil comprises from about 8.0% to about 12.0% of the composition. An optimum concentration of lanolin oil is about 10.60% of the composition.

Cetyl alcohol can comprise from about 1.0% to about 8.0% of the composition. A preferred concentration of cetyl alcohol is from about 2.0% to about 7.0% of the composition. An optimum concentration of cetyl alcohol is about 4.20% of the composition.

Stearyl alcohol can comprise from about 0.5% to about 6.0% of the composition. A preferred concentration of stearyl alcohol is from about 0.75% to about 5.0% of the composition. An optimum concentration of stearyl alcohol is about 1.50% of the composition.

Cod liver oil can comprise from about 1.0% to about 7.0% of the composition. Preferably, cod liver oil comprises from about 1.0% to about 4.0% of the composition. An optimum concentration of cod liver oil is about 2.00% of the composition.

Butylated hydroxytoluene can comprise from about 0.10% to about 1.0% of the composition. Preferably, butylated hydroxytoluene comprises from about 0.20% to about 0.80% of the composition. An optimum concentration of butylated hydroxytoluene is about 0.50% of the composition.

Methylparaben can comprise from about 0.10% to about 0.50% of the composition. A preferred concentration of methylparaben is from about 0.15% to about 0.40% of the composition. An optimum concentration of methylparaben is about 0.30% of the composition.

Propylparaben can comprise from about 0.10% to about 0.50% of the composition. Preferably, propylparaben comprises from about 0.15% to about 0.40% of the composition. An optimum concentration of propylparaben is about 0.25% of the composition.

Diazolidinyl urea can comprise from about 0.05% to about 0.25% of the composition. Preferably, diazolidinyl urea comprises from about 0.10% to about 0.20% of the composition. An optimum concentration of diazolidinyl urea is about 0.15% of the composition.

Allantoin can comprise from about 0.50% to about 2.0% of the composition. A preferred concentration of allantoin is from about 1.0% to about 2.0% of the composition. An optimum concentration of allantoin is about 1.50% of the composition.

Fragrance can comprise from about 0.05% to about 0.50% of the composition. Preferably, fragrance comprises from about 0.10% to about 0.40% of the composition. An optimum concentration of fragrance is about 0.20% of the composition. As indicated above, fragrance can be omitted, and it may be desirable to omit fragrance in circumstances in which the composition is intended for use on sensitive individuals or individuals who may undergo an allergic reaction to fragrance.

Triethanolamine can comprise from about 0.05% to about 3.0% of the composition to adjust the pH. A preferred concentration of triethanolamine is from about 0.20% to about 2.0% of the composition. An optimum concentration of triethanolamine is about 0.80% of the composition.

In another alternative embodiment of a method according to the present invention, the emulsifier of the composition can be an anionic emulsifier that is substantially hydrophilic and is soluble in water. In this embodiment, the anionic emulsifier replaces the polyethylene glycol ester of stearic acid. The composition further includes the acidic anionic polymer such as carboxypolymethylene. Optionally, but preferably, the composition includes the carbohydrate polymer such as galactoarabinan.

The anionic emulsifier that is substantially hydrophilic and soluble in water can be selected from the group consisting of sodium lauryl sulfate, sodium laureth sulfate, sodium oleyl succinate, sodium dodecylbenzenesulfonate, and sodium lauryl sarcosinate. A particularly preferred anionic emulsifier is sodium lauryl sulfate.

Commercially available preparations of sodium lauryl sulfate contain sufficient excess sodium hydroxide so that they have a pH of about 10.0. This sodium hydroxide can be used to adjust the pH when the anionic emulsifier is sodium lauryl sulfate; in this alternative, no additional alkali may be needed. When another anionic emulsifier is used, additional alkali may be required to adjust the pH.

In yet another alternative embodiment of a method according to the present invention, the emulsifier system of the composition used in the method comprises the acidic anionic polymer as described above and a nonionic emulsifier that is an ethoxylated ether or an ethoxylated ester whose carbon chain length ranges from 8 to 22 carbon atoms.

Preferably, the acidic anionic polymer is carboxypolymethylene as described above.

This alternative of the composition used in the method can further include glyceryl stearate in the emulsifier system.

The composition has a pH from about 3.0 to 6.0, adjusted as necessary, typically with an acid. The acid can be an organic acid, an inorganic acid, or a mixture of both. Preferably, the composition has a pH from about 5.0 to about 6.0.

This embodiment of the composition can further comprise a carbohydrate polymer such as galactoarabinan as described above.

In the composition, preferred organic acids include organic acids whose carbon chain length ranges from 2 to 22 carbon atoms and can be monocarboxylic, dicarboxylic, or tricarboxylic acids. The acids can be aliphatic or aromatic. Particularly preferred organic acids include citric acid, ascorbic acid, glycolic acid, lactic acid, benzoic acid, and salicylic acid. A most particularly preferred organic acid is citric acid.

Typically, in the composition, the inorganic acid is a strong acid. It can be a monoprotic, diprotic, or triprotic acid. Particularly preferred inorganic acids include hydrochloric acid, sulfuric acid, and phosphoric acid.

The composition can further include other ingredients as described above, including an emollient component, an antioxidant, a solvent component, a chelating agent, herbal extracts, a preservative, and fragrance.

In particular, the composition can further include at least one of:

(1) an emollient component comprising at least one emollient selected from the group consisting of lanolin oil, cetyl alcohol, stearyl alcohol, cod liver oil;

(2) butylated hydroxytoluene;

(3) at least one herbal extract selected from the group consisting of St. John's wort extract, witch hazel extract, chamomile extract, and arnica extract;

(4) a preservative component comprising at least one preservative selected from the group consisting of methylparaben, propylparaben and diazolidinyl urea;

(5) tetrasodium EDTA; and (6) a solvent component comprising at least one solvent selected from the group consisting of propylene glycol, butylene glycol, and glycerin.

The composition can further include other components, such as proteins, humectants, other preservatives, essential oils, other vitamins, colorants, hydroxyacids, other plant extracts, sunscreens, sodium hyaluronate, lipids, fatty acids, thickeners, panthenol, and the like. The use of such components is conventional in the cosmetic art and in the over-the-counter drug art. Typical sunscreens are octyl methoxycinnamate and benzophenone-3.

In yet another embodiment of a method according to the present invention, the emulsifier system of the composition used in the method comprises the acidic anionic polymer described above; one example of this acidic anionic polymer is marketed as Carbomer. In this embodiment, the pH is adjusted with an organic or inorganic base to a value within a range of from about 3.0 to about 6.0. Preferably, the pH of the composition is from about 5.0 to about 5.5. A preferred organic base is triethanolamine. A preferred inorganic base is sodium hydroxide. In general, it is preferred to use an organic base such as triethanolamine.

The composition used in this embodiment of the method can further comprise other ingredients. For example, the composition can further comprise a solvent component. Typically, the solvent component includes at least one solvent selected from the group consisting of propylene glycol, glycerin, or butylene glycol. Preferably, the solvent component is propylene glycol.

The composition can further comprise an emollient component. The emollient component can comprise at least one solvent selected from the group consisting of lanolin oil, cetyl alcohol, and cod liver oil. Preferably, the emollient component comprises all of lanolin oil, cetyl alcohol, and cod liver oil.

The composition can also include an antioxidant to prevent rancidity of ingredients such as cod liver oil. A preferred antioxidant is butylated hydroxytoluene (BHT).

The composition can further comprise a preservative component. The preservative component can comprise at least one preservative selected from the group consisting of methylparaben and propylparaben. Preferably, the preservative component comprises both methylparaben and propylparaben.

The composition can further include fragrance as described above. The stability and function of the cream is not altered by the presence or absence of fragrance. As indicated above, it may be desirable to omit fragrance in some cases.

The following discussion describes ranges, preferred concentrations and optimum concentrations for preferred compositions with a pH of from about 5.0 to about 5.5 according to this embodiment of the method of the present invention.

Water can comprise from about 50.0% to about 90.0% of the composition. Preferably, water comprises from about 60.0% to about 80.0% of the composition. An optimum concentration of water is about 73.55% of the composition.

The carboxypolymethylene polymer can comprise from about 0.40% to about 3.0% of the composition. Preferably, the carboxypolymethylene polymer comprises from about 0.5% to about 2.0% of the composition. An optimum concentration of the carboxypolymethylene polymer is about 1.00% of the composition.

Propylene glycol can comprise from about 2.0% to about 9.0% of the composition. Preferably, the propylene glycol comprises from about 4.0% to about 7.0% of the composition. An optimum concentration of the propylene glycol is about 5.70% of the composition.

Lanolin oil can comprise from about 5.0% to about 15.0% of this embodiment of the composition. Preferably, lanolin oil comprises from about 8.0% to about 12.0% of this embodiment of the composition. An optimum concentration of lanolin oil is about 10.00% of this embodiment of the composition.

Cetyl alcohol can comprise from about 1.0% to about 8.0% of the composition. Preferably, cetyl alcohol comprises from about 2.0% to about 7.0% of the composition. An optimum concentration of cetyl alcohol is about 3.00% of the composition.

Cod liver oil can comprise from about 1.0% to about 7.0% of the composition. Preferably, cod liver oil comprises from about 1.0% to about 4.0% of the composition. An optimum concentration of cod liver oil is about 2.00% of the composition.

Butylated hydroxytoluene can comprise from about 0.10% to about 1.0% of the composition. Preferably, butylated hydroxytoluene comprises from about 0.30% to about 0.80% of the composition. An optimum concentration of butylated hydroxytoluene is about 0.50% of the composition.

Methylparaben can comprise from about 0.10% to about 0.50% of the composition. Preferably, methylparaben comprises from about 0.15% to about 0.40% of the composition. An optimum concentration of methylparaben is about 0.30% of the composition.

Propylparaben can comprise from about 0.10% to about 0.50% of the composition. Preferably, propylparaben comprises from about 0.15% to about 0.40% of the composition. An optimum concentration of propylparaben is about 0.25% of the composition.

Allantoin can comprise from about 0.50% to about 2.0% of the composition. Preferably, allantoin comprises from about 1.0% to about 2.0% of the composition. An optimum concentration of allantoin is about 1.50% of the composition.

Fragrance, if present, can comprise from about 0.05% to about 0.50% of the composition. Preferably, if present, fragrance comprises from about 0.10% to about 0.40% of the composition. An optimum concentration of fragrance, if present, is about 0.20% of the composition.

Triethanolamine, as a 95% solution, can comprise from about 0.05% to about 3.0% of the composition to adjust the pH to a value in the range of from about 5.0 to about 5.5. Preferably, triethanolamine comprises from about 0.20% to about 2.0% of the composition to adjust the pH as indicated. An optimum concentration of triethanolamine is about 0.80% of the composition to adjust the pH as indicated.

Yet another embodiment of a method according to the present invention employs a composition comprising an oil-in-water emulsion comprising:

(1) allantoin; and
(2) an emulsifier system comprising:
    (a) cetyl alcohol; and
    (b) stearic acid.

In this embodiment, the pH of the composition is adjusted to a value within a range of from about 3.0 to about 6.0 by addition of a quantity of a weak organic base. Preferably, the pH of the composition is from about 5.0 to about 5.8. The weak organic base can be an amine-containing base such as ethanolamine, diethanolamine, or triethanolamine. A preferred organic base is triethanolamine.

The composition used in this embodiment of a method according to the present invention can further comprise other ingredients. For example, the composition can further comprise a solvent component. Typically, the solvent component includes at least one solvent selected from the group consisting of propylene glycol, glycerin, and butylene glycol. Preferably, the solvent component is propylene glycol.

The composition can further comprise an emollient component. The emollient component can comprise at least one solvent selected from the group consisting of lanolin oil, cetyl alcohol, and cod liver oil. Preferably, the emollient component comprises all of lanolin oil, cetyl alcohol, and cod liver oil.

The composition can also include an antioxidant. A preferred antioxidant is butylated hydroxytoluene.

The composition can further comprise a preservative component. The preservative component can comprise at least one preservative selected from the group consisting of methylparaben and propylparaben. Preferably, the preservative component comprises both methylparaben and propylparaben.

The composition can further include fragrance as described above. The stability and function of the cream is not altered by the presence or absence of fragrance. As indicated above, it may be desirable to omit fragrance in some cases.

The following discussion describes ranges, preferred concentrations and optimum concentrations for preferred compositions with a pH of from about 5.0 to about 5.8 according to this embodiment of a method of the present invention.

Water can comprise from about 50.0% to about 90.0% of the composition. Preferably, water comprises from about 60.0% to about 85.0% of the composition. An optimum concentration of water is about 71.70% of the composition.

Propylene glycol can comprise from about 2.0% to about 9.0% of the composition. Preferably, propylene glycol comprises from about 4.0% to about 7.0% of the composition. An optimum concentration of propylene glycol is about 5.70% of the composition.

Triethanolamine can comprise from about 0.2% to about 4.0% of the composition. Preferably, triethanolamine comprises from about 0.5% to about 3.0% of the composition. An optimum concentration of triethanolamine is about 1.25% of the composition.

Lanolin oil can comprise from about 5.0% to about 15.0% of the composition. Preferably, lanolin oil comprises from about 8.0% to about 12.0% of the composition. An optimum concentration of lanolin oil is about 10.60% of the composition.

Cetyl alcohol can comprise from about 1.0% to about 7.0% of the composition. Preferably, cetyl alcohol comprises from about 2.0% to about 6.0% of the composition. An optimum concentration of cetyl alcohol is about 3.50% of the composition.

Stearic acid can comprise from about 0.50% to about 5.0% of the composition. Preferably, stearic acid comprises from about 1.0% to about 4.0% of the composition. An optimum concentration of stearic acid is about 2.50% of the composition.

Cod liver oil can comprise from about 1.0% to about 7.0% of the composition. Preferably, cod liver oil comprises from about 1.50% to about 5.0% of the composition. An optimum concentration of cod liver oil is about 2.00% of the composition.

Butylated hydroxytoluene can comprise from about 0.1% to about 1.0% of the composition. Preferably, butylated hydroxytoluene comprises from about 0.2% to about 0.8% of the composition. An optimum concentration of butylated hydroxytoluene is about 0.5% of the composition.

Methylparaben can comprise from about 0.10% to about 0.50% of the composition. Preferably, methylparaben comprises from about 0.15% to about 0.40% of the composition. An optimum concentration of methylparaben is about 0.30% of the composition.

Propylparaben can comprise from about 0.10% to about 0.50% of the composition. Preferably, propylparaben comprises from about 0.15% to about 0.40% of the composition. An optimum concentration of propylparaben is about 0.25% of the composition.

Allantoin can comprise from about 0.50% to about 2.0% of the composition. Preferably, allantoin comprises from about 1.0% to about 2.0% of the composition. An optimum concentration of allantoin is about 1.50% of the composition.

If present, fragrance can comprise from about 0.05% to about 0.50% of the composition. Preferably, fragrance comprises from about 0.10% to about 0.40% of the composition. An optimum concentration of fragrance is about 0.20% of the composition.

Still another embodiment of a method according to the present invention employs a composition comprising an oil-in-water emulsion comprising:

(1) allantoin; and
(2) an emulsifier system comprising:
   (a) sodium stearoyl lactylate;
   (b) sodium isostearoyl lactylate;
   (c) optionally, triethanolamine stearate;
   (d) optionally, at least one nonionic emulsifier selected from the group consisting of a nonionic emulsifier that is an ethoxylated ether or an ethoxylated ester whose carbon chain length ranges from 8 to 22 carbon atoms.

Sodium stearoyl lactylate is the sodium salt of the stearic acid ester of lactyl lactate. Sodium isostearoyl lactylate is the sodium salt of the isostearic acid ester of lactyl lactate.

In the composition used in this embodiment of a method according to the present invention, the composition further comprises an acid to adjust the pH to a value in a range of from about 3.0 to about 6.0. Preferably, the composition has a pH of from about 5.0 to about 5.8. The acid can be an inorganic or an organic acid as described above. Preferably, the acid is a weak organic acid. Most preferably, the acid is citric acid.

The composition can further comprise other ingredients. For example, the composition can further comprise a solvent component. Typically, the solvent component includes at least one solvent selected from the group consisting of propylene glycol, glycerin, and butylene glycol. Preferably, the solvent component is propylene glycol.

The composition can further comprise an emollient component. The emollient component can comprise at least one emollient selected from the group consisting of lanolin oil, cetyl alcohol, and cod liver oil. Preferably, the emollient component comprises all of lanolin oil, cetyl alcohol, and cod liver oil.

The composition can also include an antioxidant. A preferred antioxidant is butylated hydroxytoluene.

The composition can further comprise a chelator component. Preferably, the chelator component is tetrasodium ethylenediaminetetraacetic acid.

The composition can further comprise a preservative component. The preservative component can comprise at least one preservative selected from the group consisting of methylparaben and propylparaben. Preferably, the preservative component comprises both methylparaben and propylparaben.

The composition can further include fragrance as described above. The stability and function of the cream is not altered by the presence or absence of fragrance. As indicated above, it may be desirable to omit fragrance in some cases.

The following discussion describes ranges, preferred concentrations and optimum concentrations for preferred compositions with a pH of from about 5.0 to about 5.8 according to this embodiment of a method according to the present invention.

Water can comprise from about 50.0% to about 90.0% of the composition. Preferably, water comprises from about 60.0% to about 80.0% of the composition. An optimum concentration of water is about 73.72% of the composition.

Propylene glycol can comprise from about 2.0% to about 9.0% of the composition. Preferably, propylene glycol comprises from about 4.0% to about 7.0% of the composition. An optimum concentration of propylene glycol is about 5.70% of the composition.

Citric acid can comprise from about 0.05% to about 0.50% of the composition. Preferably, citric acid comprises from about 0.10% to about 0.40% of the composition. An optimum concentration of citric acid is about 0.18% of the composition.

Sodium stearoyl lactylate can comprise from about 0.30% to about 3.0% of the composition. Preferably, sodium stearoyl lactylate comprises from about 0.50% to about 2.50% of the composition. An optimum concentration of sodium stearoyl lactylate is about 1.00% of the composition.

Sodium isostearoyl lactylate can comprise from about 0.05% to about 1.0% of the composition. Preferably, sodium isostearoyl lactylate comprises from about 0.10% to about 0.70% of the composition. An optimum concentration of sodium isostearoyl lactylate is about 0.25% of the composition.

Tetrasodium EDTA can comprise from about 0.05% to about 0.25% of the composition. Preferably, tetrasodium EDTA comprises from about 0.10% to about 0.20% of the composition. An optimum concentration of tetrasodium EDTA is about 0.15% of the composition.

Lanolin oil can comprise from about 5.0% to about 15.0% of the composition. Preferably, lanolin oil comprises from about 8.0% to about 12.0% of the composition. An optimum concentration of lanolin oil is about 10.60% of the composition.

Cetyl alcohol can comprise from about 1.0% to about 8.0% of the composition. Preferably, cetyl alcohol comprises from about 2.0% to about 7.0% of the composition. An optimum concentration of cetyl alcohol is about 3.80% of the composition.

Cod liver oil can comprise from about 1.0% to about 7.0% of the composition. Preferably, cod liver oil comprises from about 1.0% to about 4.0% of the composition. An optimum concentration of cod liver oil is about 2.00% of the composition.

Butylated hydroxytoluene can comprise from about 0.10% to about 1.0% of the composition. Preferably, butylated hydroxytoluene comprises from about 0.20% to about 0.80% of the composition. An optimum concentration of butylated hydroxytoluene is about 0.50% of the composition.

Methylparaben can comprise from about 0.10% to about 0.50% of the composition. Preferably, methylparaben comprises from about 0.15% to about 0.40% of the composition. An optimum concentration of methylparaben is about 0.30% of the composition.

Propylparaben can comprise from about 0.10% to about 0.50% of the composition. Preferably, propylparaben comprises from about 0.15% to about 0.40% of the composition. An optimum concentration of propylparaben is about 0.25% of the composition.

Allantoin can comprise from about 0.50% to about 2.0% of the composition. Preferably, allantoin comprises from about 1.0% to about 2.0% of this embodiment of the composition. An optimum concentration of allantoin is about 1.50% of this embodiment of the composition.

If present, fragrance can comprise from about 0.05% to about 0.50% of the composition. Preferably, fragrance comprises from about 0.10% to about 0.40% of the composition. An optimum concentration of fragrance is about 0.20% of the composition.

Still another embodiment of a method according to the present invention uses a composition comprising an oil-in-water emulsion comprising:

(1) allantoin; and
(2) an emulsifier system comprising at least one polyethyleneglycol ether of cetearyl alcohol.

In polyethylene glycol ethers of cetearyl alcohol suitable for use in compositions according to this embodiment of methods of the present invention, the number of ethylene glycol moieties can range from 6 to 40, e.g., $R(OCH_2CH_2)_{25}OH$ where $R=CH_3(CH_2)_{16-18}$. In one preferred embodiment of compounds of the present invention, the emulsifier system comprises both ceteareth-25 and ceteareth-6, i.e., polyethylene glycol ethers of cetearyl alcohol with 25 and 6 ethylene glycol units respectively.

In this embodiment of a method according to the present invention, the composition further comprises an acid to adjust the pH to a value within a range of from about 3.0 to about 6.0. Preferably, the pH of the composition is from about 5.0 to about 5.8. The acid can be an inorganic or an organic acid as described above. Preferably, the acid is a weak organic acid. Most preferably, the acid is citric acid.

The composition can further comprise other ingredients. For example, the composition can further comprise a solvent component. Typically, the solvent component is selected from the group consisting of propylene glycol, glycerin, or butylene glycol. Preferably, the solvent component is propylene glycol.

The composition can further comprise a chelator component. Preferably, the chelator component is tetrasodium ethylenediaminetetraacetic acid.

The composition can further comprise an emollient component. The emollient component can comprise at least one emollient selected from the group consisting of lanolin oil, cetyl alcohol, stearyl alcohol, and cod liver oil. Preferably, the emollient component comprises all of lanolin oil, cetyl alcohol, stearyl alcohol, and cod liver oil.

The composition can also further comprise an antioxidant. A preferred antioxidant is butylated hydroxytoluene.

The composition can further comprise a preservative component. The preservative component can comprise at least one preservative selected from the group consisting of methylparaben, propylparaben, and diazolidinyl urea. Preferably, the preservative component comprises all of methylparaben, propylparaben, and diazolidinyl urea.

The composition can further include fragrance as described above. The stability and function of the cream is not altered by the presence or absence of fragrance. As indicated above, it may be desirable to omit fragrance in some cases.

The following discussion describes ranges, preferred concentrations and optimum concentrations for preferred compositions with a pH of from about 5.0 to about 5.8 according to this embodiment of a method according to the present invention.

Water can comprise from about 50.0% to about 90.0% of the composition. Preferably, water comprises from about 55.0% to about 75.0% of the composition. An optimum concentration of water is about 66.33% of the composition.

Propylene glycol can comprise from about 2.0% to about 9.0% of the composition. Preferably, propylene glycol comprises from about 4.2% to about 7.0% of the composition. An optimum concentration of propylene glycol is about 5.70% of the composition.

Tetrasodium EDTA can comprise from about 0.05% to about 0.50% of the composition. Preferably, tetrasodium EDTA comprises from about 0.10% to about 0.30% of the composition. An optimum concentration of tetrasodium EDTA is about 0.15% of the composition.

Ceteareth-25 can comprise from about 0.50% to about 4.0% of the composition. Preferably, ceteareth-25 comprises from about 2.0% to about 3.5% of the composition. An optimum concentration of ceteareth-25 is about 2.60% of the composition.

Citric acid can comprise from about 0.04% to about 0.40% of the composition. Preferably, citric acid comprises from about 0.10% to about 0.30% of the composition. An optimum concentration of citric acid is about 0.12% of the composition.

Lanolin oil can comprise from about 5.0% to about 15.0% of the composition. Preferably, lanolin oil comprises from about 8.0% to about 12.0% of the composition. An optimum concentration of lanolin oil is about 10.60% of the composition.

Cetyl alcohol can comprise from about 3.0% to about 10.0% of the composition. Preferably, cetyl alcohol comprises from about 3.5% to about 7.5% of the composition. An optimum concentration of cetyl alcohol is about 4.30% of the composition.

Stearyl alcohol can comprise from about 1.0% to about 5.0% of the composition. Preferably, stearyl alcohol comprises from about 2.0% to about 4.0% of the composition. An optimum concentration of stearyl alcohol is about 3.50% of the composition.

Ceteareth-6 can comprise from about 0.5% to about 4.0% of the composition. Preferably, ceteareth-6 comprises from about 1.0% to about 3.0% of the composition. An optimum concentration of ceteareth-6 is about 1.80% of the composition.

Cod liver oil can comprise from about 1.0% to about 7.0% of the composition. Preferably, cod liver oil comprises from about 1.0% to about 4.0% of the composition. An optimum concentration of cod liver oil is about 2.00% of the composition.

Butylated hydroxytoluene can comprise from about 0.10% to about 1.0% of the composition. Preferably, butylated hydroxytoluene comprises from about 0.20% to about 0.80% of the composition. An optimum concentration of butylated hydroxytoluene is about 0.50% of the composition.

Methylparaben can comprise from about 0.10% to about 0.50% of the composition. Preferably, methylparaben comprises from about 0.15% to 0.40% of the composition. An optimum concentration of methylparaben is about 0.30% of the composition.

Propylparaben can comprise from about 0.10% to about 0.50% of the composition. Preferably, propylparaben comprises from about 0.15% to about 0.40% of the composition. An optimum concentration of propylparaben is about 0.25% of the composition.

Diazolidinyl urea can comprise from about 0.05% to about 0.50% of the composition. Preferably, diazolidinyl urea comprises from about 0.10% to about 0.30% of the composition. An optimum concentration of diazolidinyl urea is about 0.15% of the composition.

Allantoin can comprise from about 0.50% to about 2.0% of the composition. Preferably, allantoin comprises from about 1.0% to about 2.0% of the composition. A preferred concentration of allantoin is about 1.50% of the composition.

If present, fragrance can comprise from about 0.05% to about 0.50% of the composition. Preferably, fragrance comprises from about 0.10% to about 0.40% of the composition. An optimum concentration of fragrance is about 0.20% of the composition.

Yet another embodiment of a method according to the present invention uses a composition comprising an oil-in-water emulsion comprising:

(1) allantoin; and
(2) an emulsifier system comprising:
   (a) a polyethylene glycol ester of stearic acid; and
   (b) glyceryl stearate.

Typically, the number of ethylene glycol moieties in the polyethylene glycol ester of stearic acid is from 25 to 100. Two preferred polyethylene glycol esters of stearic acid for use in compositions suitable for use in this embodiment of a method according to the present invention are PEG-40 stearate and PEG-100 stearate, with 40 and 100 ethylene glycol moieties respectively. A particularly preferred polyethylene glycol ester of stearic acid is PEG-100 stearate.

In this embodiment of a method according to the present invention, the composition further comprises an acid to adjust the pH to a value in a range of from about 3.0 to about 6.0. Preferably, the pH of the composition is from about 5.0 to about 5.8. The acid can be an inorganic or an organic acid as described above. Preferably, the acid is a weak organic acid. Most preferably, the acid is citric acid.

The composition can further comprise other ingredients. For example, the composition can further comprise a solvent component. Typically, the solvent component includes at least one solvent selected from the group consisting of propylene glycol, glycerin, and butylene glycol. Preferably, the solvent component is propylene glycol.

The composition can further comprise a chelator component. Preferably, the chelator component is tetrasodium ethylenediaminetetraacetic acid.

The composition can further comprise an emollient component. The emollient component can comprise at least one emollient selected from the group consisting of lanolin oil, cetyl alcohol, stearyl alcohol, and cod liver oil. Preferably, the emollient component comprises all of lanolin oil, cetyl alcohol, stearyl alcohol, and cod liver oil.

The composition can also further comprise an antioxidant. A preferred antioxidant is butylated hydroxytoluene.

The composition can further comprise a preservative component. The preservative component can comprise at least one preservative selected from the group consisting of methylparaben, propylparaben, and diazolidinyl urea. Preferably, the preservative component comprises all of methylparaben, propylparaben, and diazolidinyl urea.

The composition can further include fragrance as described above. The stability and function of the cream is not altered by the presence or absence of fragrance. As indicated above, it may be desirable to omit fragrance in some cases.

The following discussion describes ranges, preferred concentrations and optimum concentrations for preferred compositions with a pH of from about 5.0 to about 5.8 useful in methods of this embodiment of the present invention.

Water can comprise from about 50.0% to about 90.0% of the composition. Preferably, water comprises from about 55.0% to about 80.0% of the composition. An optimum concentration of water is about 67.86% of the composition.

Propylene glycol can comprise from about 2.00% to about 9.00% of the composition. Preferably, propylene glycol comprises from about 4.30% to about 7.00% of the composition. An optimum concentration of propylene glycol is about 5.70% of the composition.

Tetrasodium EDTA can comprise from about 0.05% to about 0.50% of the composition. Preferably, PEG-100 stearate comprises from about 1.50% to about 3.00% of the composition. An optimum concentration of PEG-100 stearate is about 2.60% of the composition.

Lanolin oil can comprise from about 5.0% to about 15.0% of the composition. Preferably, lanolin oil comprises from about 8.0% to about 12.0% of the composition. An optimum concentration of lanolin oil is about 10.60% of the composition.

Cetyl alcohol can comprise from about 2.0% to about 10.0% of the composition. Preferably, cetyl alcohol comprises from about 2.50% to about 7.50% of the composition. An optimum concentration of cetyl alcohol is about 3.00% of the composition.

Stearyl alcohol can comprise from about 1.0% to about 4.0% of the composition. Preferably, stearyl alcohol comprises from about 1.0% to about 3.5% of the composition. An optimum concentration of stearyl alcohol is about 2.50% of the composition.

Glyceryl stearate can comprise from about 1.0% to about 5.0% of the composition. Preferably, glyceryl stearate comprises from about 2.0% to about 4.0% of the composition. An optimum concentration of glyceryl stearate is about 2.50% of the composition.

Cod liver oil can comprise from about 1.0% to about 7.0% of the composition. Preferably, cod liver oil comprises from about 1.0% to about 4.0% of the composition. An optimum concentration of cod liver oil is about 2.00% of the composition.

Butylated hydroxytoluene can comprise from about 0.10% to about 1.0% of the composition. Preferably, butylated hydroxytoluene comprises from about 0.20% to about 0.80% of the composition. An optimum concentration of butylated hydroxytoluene is about 0.50% of the composition.

Methylparaben can comprise from about 0.10% to about 0.50% of the composition. Preferably, methylparaben comprises from about 0.15% to 0.40% of the composition. An optimum concentration of methylparaben is about 0.30% of the composition.

Propylparaben can comprise from about 0.10% to about 0.50% of the composition. Preferably, propylparaben comprises from about 0.15% to about 0.40% of the composition. An optimum concentration of propylparaben is about 0.25% of the composition.

Diazolidinyl urea can comprise from about 0.05% to about 0.50% of the composition. Preferably, diazolidinyl urea comprises from about 0.10% to about 0.30% of the composition. An optimum concentration of diazolidinyl urea is about 0.20% of the composition.

Allantoin can comprise from about 0.50% to about 2.0% of the composition. Preferably, allantoin comprises from about 1.0% to about 2.0% of the composition. A preferred concentration of allantoin is about 1.50% of the composition.

If present, fragrance can comprise from about 0.05% to about 0.50% of the composition. Preferably, fragrance comprises from about 0.10% to about 0.40% of the composition. An optimum concentration of fragrance is about 0.20% of the composition.

Yet another embodiment of a method according to the present invention employs a composition comprising an oil-in-water emulsion comprising:

(1) allantoin;
(2) a carbohydrate polymer; and
(3) an emulsifier system comprising:
   (a) beeswax; and
   (b) an anionic emulsifier that is substantially hydrophilic and is soluble in water.

The carbohydrate polymer is typically selected from the group consisting of galactoarabinan, polygalactose, and polyarabinose. Preferably, the carbohydrate polymer is galactoarabinan.

The anionic emulsifier that is substantially hydrophilic and soluble in water can be selected from the group consisting of sodium lauryl sulfate, sodium laureth sulfate, sodium oleyl succinate, sodium dodecylbenzenesulfonate, and sodium lauryl sarcosinate. A particularly preferred anionic emulsifier is sodium lauryl sulfate.

The pH of the composition is adjusted to a value in a range of between about 3.0 and about 6.0, typically with an acid. Preferably, the pH of the composition is from about 5.0 to about 6.0. The acid can be an inorganic or an organic acid as described above. Preferably, the acid is a weak organic acid. Most preferably, the acid is citric acid.

The composition used in this embodiment of a method according to the present invention can further comprise other ingredients. For example, the composition can further comprise a solvent component. Typically, the solvent component comprises at least one solvent selected from the group consisting of propylene glycol, glycerin, and butylene glycol. Preferably, the solvent component is propylene glycol.

The composition can further comprise a chelator component. Preferably, the chelator component is tetrasodium ethylenediaminetetraacetic acid.

The composition can further comprise an emollient component. The emollient component can comprise at least one emollient selected from the group consisting of lanolin oil, cetyl alcohol, stearyl alcohol, and cod liver oil. Preferably, the emollient component comprises all of lanolin oil, cetyl alcohol, stearyl alcohol, and cod liver oil The composition can also further comprise an antioxidant. A preferred antioxidant is butylated hydroxytoluene.

The composition can further comprise a preservative component. The preservative component can comprise at least one preservative selected from the group consisting of methylparaben or propylparaben. Preferably, the preservative component comprises methylparaben and propylparaben.

The composition can further include fragrance as described above. The stability and function of the cream is not altered by the presence or absence of fragrance. As indicated above, it may be desirable to omit fragrance in some cases.

The following discussion describes ranges, preferred concentrations and optimum concentrations for preferred compositions with a pH of from about 5.0 to about 6.0 according to this embodiment of a method according to the present invention.

Water can comprise from about 50.0% to about 90.0% of the composition. Preferably, water comprises from about 60.0% to about 80.0% of the composition. An optimum concentration of water is about 61.65% of the composition.

Propylene glycol can comprise from about 2.0% to about 9.0% of the composition. Preferably, propylene glycol comprises from about 4.0% to about 7.0% of the composition. An optimum concentration of propylene glycol is about 5.70% of the composition.

Sodium lauryl sulfate, as a 30% solution, can comprise from about 0.50% to about 5.0% of the composition. Preferably, sodium lauryl sulfate, as a 30% solution, comprises from about 1.0% to about 3.0% of the composition. An optimum concentration of sodium lauryl sulfate, as a 30% solution, is about 1.90% of the composition.

Tetrasodium EDTA can comprise from about 0.05% to about 0.30% of the composition. Preferably, tetrasodium EDTA comprises from about 0.10% to about 0.20% of the composition. An optimum concentration of tetrasodium EDTA is about 0.15% of the composition.

Galactoarabinan can comprise from about 1.0% to about 25.0% of the composition. Preferably, galactoarabinan comprises from about 3.0% to about 15.0% of the composition. An optimum concentration of galactoarabinan is about 5.00% of the composition.

Citric acid can comprise from about 0.05% to about 0.25% of the composition. Preferably, citric acid comprises from about 0.10% to about 0.20% of the composition. An optimum concentration of citric acid is about 0.15% of the composition.

Lanolin oil can comprise from about 5.0% to about 15.0% of the composition. Preferably, lanolin oil comprises from about 8.0% to about 12.0% of the composition. An optimum concentration of lanolin oil is about 10.60% of the composition.

Cetyl alcohol can comprise from about 1.0% to about 8.0% of the composition. Preferably, cetyl alcohol comprises from about 2.0% to about 7.0% of the composition. An optimum concentration of cetyl alcohol is about 4.20% of the composition.

Stearyl alcohol can comprise from about 0.50% to about 6.0% of the composition. Preferably, stearyl alcohol comprises from about 1.0% to about 4.0% of the composition. An optimum concentration of stearyl alcohol is about 2.00% of the composition.

Beeswax can comprise from about 0.50% to about 5.0% of the composition. Preferably, beeswax comprises from about 1.0% to about 3.0% of the composition. An optimum concentration of beeswax is about 1.90% of the composition.

Cod liver oil can comprise from about 0.50% to about 15.0% of the composition. Preferably, cod liver oil comprises from about 1.0% to about 10.0% of the composition. An optimum concentration of cod liver oil is about 2.00% of the composition.

Butylated hydroxytoluene can comprise from about 0.1% to about 3.0% of the composition. Preferably, butylated hydroxytoluene comprises from about 0.25% to about 2.50% of the composition. An optimum concentration of butylated hydroxytoluene is about 0.50% of the composition.

Methylparaben can comprise from about 0.10% to about 0.50% of the composition. Preferably, methylparaben comprises from about 0.15% to about 0.40% of the composition. An optimum concentration of methylparaben is about 0.30% of the composition.

Propylparaben can comprise from about 0.10% to about 0.50% of the composition. Preferably, propylparaben comprises from about 0.15% to about 0.40% of the composition. An optimum concentration of propylparaben is about 0.25% of the composition.

Allantoin can comprise from about 0.50% to about 2.0% of the composition. Preferably, allantoin comprises from about 1.0% to about 2.0% of the composition. An optimum concentration of allantoin is about 1.50% of the composition.

If present, fragrance can comprise from about 0.05% to about 0.50% of the composition. Preferably, if present, fragrance can comprise from about 0.10% to about 0.40% of the composition. An optimum concentration of fragrance is about 0.20% of the composition.

The compositions are prepared by standard mixing techniques, such as are conventional in the cosmetic art and in the art of over-the-counter drug formulation for blending lipid-soluble components and water-soluble components. These mixing techniques include both manual and mechanical mixing, and include homogenization mixing and sweep mixing. The mixing techniques to be used can be chosen by one of ordinary skill in the art based on variables such as the viscosity of the components to be mixed and the volume of those components, as well as the relative proportion of lipid-soluble and water-soluble ingredients. The compositions can be mixed in two or more batches, such as one batch containing lipid-soluble ingredients and another batch containing water-soluble ingredients, and the batches can then be mixed at the final stage of preparation. In some cases, if triethanolamine is used, it is added last, as otherwise it may tend to thicken the emulsion. Other preparation methods are known in the art.

The dosages of the allantoin-containing composition to be administered and the frequency of those dosages can be determined by one of ordinary skill in the art depending on the particular disease affecting the patient, the clinical severity of the disease, the age and weight of the patient, the exposure of the patient to conditions that may precipitate outbreaks of dermatological or systemic inflammatory conditions, the degree of exposure to environmental insults, other drugs being administered, the response of the patient, and other pharmacokinetic factors generally understood in the art, such as liver and kidney metabolism. The interrelationship of dosages for animals of various sizes and species and humans based on $mg/m^3$ of surface area is described in E. J. Freireich et al., "Quantitative Comparison of Toxicity of Anticancer Agents in Mouse, Rat, Hamster, Dog, Monkey and Man," Cancer Chemother. Rep. 50:219–244 (1966).

Adjustments in the dosage regimen can be made to optimize the therapeutic response. Doses can be divided and administered on a daily basis or the dose can be reduced proportionately depending upon the therapeutic situation.

The allantoin-containing composition can be administered from once per day up to at least five times per day depending on the severity of the disease, the total dosage to be administered, and the judgment of the treating physician. In some cases, the allantoin-containing composition need not be administered on a daily basis, but can be administered every other day, every third day, or on other such schedules. However, it is generally preferred to administer the allantoin-containing composition daily.

In methods according to the present invention, the allantoin-containing composition can be administered alone or with other conventional therapeutic agents in a therapeutically effective quantity. These other therapeutic agents can either be applied topically to the skin or can be administered systemically, such as orally, intravenously, or by other conventional routes as generally known in the art. These agents can include steroids, nonsteroidal anti-inflammatory agents, leukotriene antagonists, monoclonal antibodies, and other agents. Additional agents can be administered to promote healing in the form of conventional creams or emulsions.

The invention is illustrated by the following Examples. These Examples are for illustrative purposes only and are not intended to limit the invention.

EXAMPLES

Example 1

Preparation of Skin Protectant Over-the-Counter Cream with pH of 7.4

(Prior Art Example)

A skin protectant over-the-counter (OTC) cream was prepared in accordance with the formulation of Table 1.

TABLE 1

COMPOSITION OF ALLANTOIN-CONTAINING SKIN CREAM WITH pH OF 7.4

| INGREDIENT | RANGE | PREFERRED | OPTIMUM |
|---|---|---|---|
| Part A | | | |
| Water | 50.0–90.0 | 55.0–75.0 | 66.20 |
| Sodium Lauryl Sulfate (30%) | 0.50–2.50 | 1.00–2.50 | 1.90 |
| Propylene Glycol | 2.0–9.0 | 3.0–6.0 | 5.30 |
| Tetrasodium EDTA | 0.05–0.50 | 0.10–0.30 | 0.15 |
| Part B | | | |
| Lanolin Oil | 5.0–15.0 | 8.0–12.0 | 10.60 |
| Cetyl Alcohol | 3.0–10.0 | 3.5–7.5 | 6.80 |
| Stearyl Alcohol | 1.0–5.0 | 1.0–3.0 | 2.00 |
| Beeswax | 0.50–2.50 | 1.0–2.5 | 1.90 |
| Cod Liver Oil | 1.0–7.0 | 1.0–4.0 | 2.00 |
| BHT | 0.10–1.00 | 0.20–0.80 | 0.50 |
| Part C | | | |
| St. John's Wort Extract | 0.05–0.50 | 0.05–0.15 | 0.10 |
| Witch Hazel Extract | 0.05–0.50 | 0.05–0.15 | 0.10 |
| Chamomile Extract | 0.05–0.50 | 0.05–0.15 | 0.10 |
| Arnica Extract | 0.05–0.50 | 0.05–0.15 | 0.10 |
| Methylparaben | 0.10–0.50 | 0.15–0.40 | 0.30 |
| Propylparaben | 0.10–0.50 | 0.10–0.30 | 0.25 |
| Allantoin | 0.50–2.00 | 0.50–2.00 | 1.50 |
| Fragrance | 0.05–0.50 | 0.10–0.30 | 0.20 |

The Part A ingredients were combined and heated to 175° F. with mixing. The Part B ingredients were combined and heated to 175° F. with mixing. The Part B mixture was then added to the Part A mixture with mixing. The resulting mixture was then cooled to 120° F. with continued mixing. The Part C ingredients were then added with mixing. The final emulsion was allowed to cool with continued mixing. The resulting cream had a pH of 7.4. Samples of the cream prepared from Example 1 were used for accelerated aging stability studies and analyzed for their allantoin concentration after a period of time at 40° C. The results are shown in Table 2.

As can be seen from Table 2, the allantoin in the cream from Example 1 undergoes degradation and would not meet the specifications required for an OTC drug.

TABLE 2

STABILITY OF ALLANTOIN IN SKIN CREAM COMPOSITION OF EXAMPLE 1 WITH STORAGE AT 40° C.

| Days at 40° C. | Weight % Allantoin |
|---|---|
| 0 | 1.5 |
| 30 | 1.4 |
| 60 | 1.3 |
| 90 | 1.2 |

Example 2

Preparation of a Cream Containing Allantoin with Lower pH

An OTC skin cream containing allantoin was prepared using the ingredients in Table 3 to provide a cream with a lower pH.

TABLE 3

COMPOSITION OF ALLANTOIN-CONTAINING SKIN CREAM WITH pH OF 5.3

| INGREDIENT | RANGE | PREFERRED | OPTIMUM |
|---|---|---|---|
| Part A | | | |
| Water | 50.0–90.0 | 55.0–75.0 | 68.68 |
| Sodium Lauryl Sulfate (30%) | 0.50–2.50 | 1.00–2.50 | 1.90 |
| Propylene Glycol | 2.0–9.0 | 3.0–6.0 | 5.30 |
| Tetrasodium EDTA | 0.05–0.50 | 0.10–0.30 | 0.15 |
| Citric Acid | 0.05–0.50 | 0.08–0.35 | 0.12 |
| Part B | | | |
| Lanolin Oil | 5.0–15.0 | 8.0–12.0 | 10.60 |
| Cetyl Alcohol | 3.0–10.0 | 3.5–7.5 | 4.20 |
| Stearyl Alcohol | 1.0–5.0 | 1.0–3.0 | 2.00 |
| Beeswax | 0.50–2.50 | 1.0–2.5 | 1.90 |
| Cod Liver Oil | 1.0–7.0 | 1.0–4.0 | 2.00 |
| BHT | 0.10–1.00 | 0.20–0.80 | 0.50 |
| Part C | | | |
| St. John's Wort Extract | 0.05–0.50 | 0.05–0.15 | 0.10 |
| Witch Hazel Extract | 0.05–0.50 | 0.05–0.15 | 0.10 |
| Chamomile Extract | 0.05–0.50 | 0.05–0.15 | 0.10 |
| Arnica Extract | 0.05–0.50 | 0.05–0.15 | 0.10 |
| Methylparaben | 0.10–0.50 | 0.15–0.40 | 0.30 |
| Propylparaben | 0.10–0.50 | 0.10–0.30 | 0.25 |
| Allantoin | 0.50–2.00 | 0.50–2.00 | 1.50 |
| Fragrance | 0.05–0.50 | 0.10–0.30 | 0.20 |

The Part A ingredients were combined and heated to 175° F. with mixing. The Part B ingredients were combined and heated to 175° F. with mixing. The Part B mixture was added to the Part A mixture with mixing. The resulting mixture was then cooled to 120° F. with mixing at which time the Part C ingredients were added with mixing. The final emulsion was allowed to cool with continue mixing. The resulting cream had a pH of 5.3.

It was found that a similar cream was produced if Part B was added to Part A or Part A was added to Part B. However, the cream has a better appearance if the oil phase and water phase are homogenized under high shear after the two phases are added to one another.

Samples of the cream of this example were used for accelerated aging stability studies and analyzed for their allantoin concentration. The results are shown in Table 4. As can be seen from Table 4, the allantoin is stable over time in a cream with a pH of 5.3.

TABLE 4

STABILITY OF ALLANTOIN IN SKIN CREAM COMPOSITION OF EXAMPLE 2 WITH STORAGE AT 40° C.

| Days at 40° C. | Weight % Allantoin |
|---|---|
| 0 | 1.4 |
| 30 | 1.4 |
| 60 | 1.4 |
| 90 | 1.4 |

Example 3

Preparation of Allantoin-Containing Skin Cream with Ionic Emulsifiers

An allantoin-containing skin cream with ionic emulsifiers is prepared according to Table 5. The preparation follows the method used in Example 2, with the ingredients in each of Part A, Part B, and Part C being combined separately and then Part B being added to Part A, with Part C then being added to the combination of Part A and Part B. The pH is adjusted to a value in a range of from about 5.0 to about 5.8 by neutralizing the stearic acid with enough triethanolamine to reach this pH. Other bases can be used instead of triethanolamine.

TABLE 5

ALLANTOIN-CONTAINING SKIN CREAM WITH IONIC EMULSIFIERS

| INGREDIENT | RANGE | PREFERRED | OPTIMUM |
|---|---|---|---|
| Part A | | | |
| Water | 50.0–90.0 | 60.0–85.0 | 71.70 |
| Propylene Glycol | 2.0–9.0 | 4.0–7.0 | 5.70 |
| Triethanolamine (99%) | 0.20–4.0 | 0.50–3.0 | 1.25 |
| Part B | | | |
| Lanolin Oil | 5.0–15.0 | 8.0–12.0 | 10.60 |
| Cetyl Alcohol | 1.0–7.0 | 2.0–6.0 | 3.50 |
| Stearic Acid | 0.50–5.0 | 1.0–4.0 | 2.50 |
| Cod Liver Oil | 1.0–7.0 | 1.5–5.0 | 2.00 |
| Butylated Hydroxytoluene | 0.10–1.0 | 0.20–0.80 | 0.50 |
| Part C | | | |
| Methylparaben | 0.10–0.50 | 0.15–0.40 | 0.30 |
| Propylparaben | 0.10–0.50 | 0.15–0.40 | 0.25 |
| Allantoin | 0.50–2.0 | 1.0–2.0 | 1.50 |
| Fragrance | 0.05–0.50 | 0.10–0.40 | 0.20 |

Example 4

Preparation of Allantoin-Containing Skin Cream with Lactylate Emulsifiers

An allantoin-containing skin cream with the emulsifiers sodium stearoyl lactylate and sodium isostearoyl lactylate is prepared according to Table 6. The preparation follows the method used in Example 3. The pH is adjusted by the addition of the appropriate quantity of citric acid.

TABLE 6

ALLANTOIN-CONTAINING SKIN CREAM WITH LACTYLATE EMULSIFIERS

| INGREDIENT | RANGE | PREFERRED | OPTIMUM |
|---|---|---|---|
| Part A | | | |
| Water | 50.0–90.0 | 60.0–80.0 | 73.42 |
| Propylene Glycol | 2.0–9.0 | 4.0–7.0 | 5.70 |
| Citric Acid | 0.05–0.50 | 0.10–0.40 | 0.18 |
| Sodium Stearoyl Lactylate | 0.30–3.0 | 0.50–2.50 | 1.00 |
| Sodium Isostearoyl Lactylate | 0.05–1.0 | 0.10–0.70 | 0.25 |
| Tetrasodium EDTA | 0.05–0.25 | 0.10–0.20 | 0.15 |
| Part B | | | |
| Lanolin Oil | 5.0–15.0 | 8.0–12.0 | 10.60 |
| Cetyl Alcohol | 1.0–8.0 | 2.0–7.0 | 3.80 |
| Cod Liver Oil | 1.0–7.0 | 1.0–4.0 | 2.00 |
| Butylated Hydroxytoluene | 0.10–1.0 | 0.20–0.80 | 0.50 |

TABLE 6-continued

ALLANTOIN-CONTAINING SKIN CREAM WITH LACTYLATE EMULSIFIERS

| INGREDIENT | RANGE | PREFERRED | OPTIMUM |
|---|---|---|---|
| Part C | | | |
| Methylparaben | 0.10–0.50 | 0.15–0.40 | 0.30 |
| Propylparaben | 0.10–0.50 | 0.15–0.40 | 0.25 |
| Allantoin | 0.50–2.0 | 1.0–2.0 | 1.50 |
| Fragrance | 0.05–0.50 | 0.10–0.40 | 0.20 |

Example 5

Preparation of Allantoin-Containing Skin Cream with Carboxypolymethylene Polymer

An allantoin-containing skin cream with carboxypolymethylene polymer is prepared according to Table 7. The preparation follows the method used in Example 3, except that the triethanolamine (Part D) is added last, after the combining of Parts A, B, and C, to avoid thickening of the emulsion. The triethanolamine is added to adjust the pH.

TABLE 7

ALLANTOIN-CONTAINING SKIN CREAM WITH CARBOXYPOLYMETHYLENE POLYMER

| INGREDIENT | RANGE | PREFERRED | OPTIMUM |
|---|---|---|---|
| Part A | | | |
| Water | 50.0–90.0 | 60.0–80.0 | 73.55 |
| Carboxypolymethylene Polymer | 0.40–3.0 | 0.50–2.0 | 1.00 |
| Propylene Glycol | 2.0–9.0 | 4.0–7.0 | 5.70 |
| Part B | | | |
| Lanolin Oil | 5.0–15.0 | 8.0–12.0 | 10.00 |
| Cetyl Alcohol | 1.0–8.0 | 2.0–7.0 | 3.00 |
| Cod Liver Oil | 1.0–7.0 | 1.0–4.0 | 2.00 |
| Butylated Hydroxytoluene | 0.10–1.0 | 0.20–0.80 | 0.50 |
| Part C | | | |
| Methylparaben | 0.10–0.50 | 0.15–0.40 | 0.30 |
| Propylparaben | 0.10–0.50 | 0.15–0.40 | 0.25 |
| Allantoin | 0.50–2.0 | 1.0–2.0 | 1.50 |
| Fragrance | 0.05–0.50 | 0.10–0.40 | 0.20 |
| Part D | | | |
| Triethanolamine (99%) | 0.05–3.0 | 0.20–2.0 | 0.80 |

Example 6

Preparation of Allantoin-Containing Skin Cream with Polyethylene Glycol Ethers of Cetearyl Alcohol

An allantoin-containing skin cream with polyethylene glycol ethers of cetearyl alcohol is prepared according to Table 8. The preparation follows the method used in Example 3. The citric acid is added to adjust the pH.

TABLE 8

ALLANTOIN-CONTAINING SKIN CREAM WITH POLYETHYLENE GLYCOL ETHERS OF CETEARYL ALCOHOL

| INGREDIENT | RANGE | PREFERRED | OPTIMUM |
|---|---|---|---|
| Part A | | | |
| Water | 50.0–90.0 | 55.0–75.0 | 66.33 |
| Propylene Glycol | 2.0–9.0 | 4.0–7.0 | 5.70 |
| Tetrasodium EDTA | 0.05–0.50 | 0.10–0.30 | 0.15 |
| Ceteareth–25 | 0.50–4.0 | 2.00–3.50 | 2.60 |
| Citric Acid | 0.04–0.40 | 0.10–0.30 | 0.12 |
| Part B | | | |
| Lanolin Oil | 5.0–15.0 | 8.0–12.0 | 10.60 |
| Cetyl Alcohol | 3.0–10.0 | 3.5–7.5 | 4.30 |
| Stearyl Alcohol | 1.0–5.0 | 2.0–4.0 | 3.50 |
| Ceteareth–6 | 0.50–4.0 | 1.0–3.0 | 1.80 |
| Cod Liver Oil | 1.0–7.0 | 1.0–4.0 | 2.00 |
| Butylated Hydroxytoluene | 0.10–1.0 | 0.20–0.80 | 0.50 |
| Part C | | | |
| Methylparaben | 0.10–0.50 | 0.15–0.40 | 0.30 |
| Propylparaben | 0.10–0.50 | 0.15–0.40 | 0.25 |
| Diazolidinyl Urea | 0.05–0.50 | 0.10–0.30 | 0.15 |
| Allantoin | 0.50–2.0 | 1.0–2.0 | 1.50 |
| Fragrance | 0.05–0.50 | 0.10–0.30 | 0.20 |

Example 7

Preparation of Allantoin-Containing Skin Cream with Polyethylene Glycol Ester of Stearic Acid and Glyceryl Stearate

An allantoin-containing skin cream with a polyethylene glycol ester of stearic acid and glyceryl stearate is prepared according to Table 9. The preparation follows the method used in Example 3. The citric acid is added to adjust the pH.

TABLE 9

ALLANTOIN-CONTAINING SKIN CREAM WITH POLYETHYLENE GLYCOL ESTER OF STEARIC ACID AND GLYCERYL STEARATE

| INGREDIENT | RANGE | PREFERRED | OPTIMUM |
|---|---|---|---|
| Part A | | | |
| Water | 50.0–90.0 | 55.0–80.0 | 67.86 |
| Propylene Glycol | 2.0–9.0 | 4.3–7.0 | 5.70 |
| Tetrasodium EDTA | 0.05–0.50 | 0.10–0.30 | 0.15 |
| Citric Acid | 0.04–0.40 | 0.10–0.30 | 0.14 |
| PEG–100 Stearate | 1.0–5.0 | 1.5–3.0 | 2.60 |
| Part B | | | |
| Lanolin Oil | 5.0–15.0 | 2.0–12.0 | 10.60 |
| Cetyl Alcohol | 3.0–10.0 | 2.5–7.5 | 3.0 |
| Stearyl Alcohol | 1.0–4.0 | 1.0–3.5 | 2.50 |
| Glyceryl Stearate | 1.0–5.0 | 2.0–4.0 | 2.50 |
| Cod Liver Oil | 1.0–7.0 | 1.0–4.0 | 2.00 |
| Butylated Hydroxytoluene | 0.10–1.0 | 0.20–0.80 | 0.50 |
| Part C | | | |
| Methylparaben | 0.10–0.50 | 0.15–0.40 | 0.30 |
| Propylparaben | 0.10–0.50 | 0.15–0.40 | 0.25 |
| Diazolidinyl Urea | 0.05–0.50 | 0.10–0.30 | 0.20 |
| Allantoin | 0.50–2.00 | 1.0–2.0 | 1.50 |
| Fragrance | 0.05–0.50 | 0.10–0.40 | 0.20 |

Example 8

Preparation of Allantoin-Containing Skin Cream with Carboxypolymethylene Polymer and Polyethylene Glycol Ester of Stearic Acid

An allantoin-containing skin cream with a carboxypolymethylene polymer and a polyethylene glycol ester of stearic acid is prepared according to Table 10. The preparation follows the method used in Example 5, with the triethanolamine (Part D) being added last. The triethanolamine is added to adjust the pH.

TABLE 10

ALLANTOIN-CONTAINING SKIN CREAM WITH A CARBOXYPOLYMETHYLENE POLYMER AND A POLYETHYLENE GLYCOL ESTER OF STEARIC ACID

| INGREDIENT | RANGE | PREFERRED | OPTIMUM |
|---|---|---|---|
| Part A | | | |
| Water | 50.0–90.0 | 60.0–85.0 | 69.95 |
| Carboxypolymethylene Polymer | 0.30–3.0 | 0.50–2.0 | 0.85 |
| Propylene Glycol | 2.0–9.0 | 4.0–7.0 | 5.70 |
| PEG-100 Stearate | 0.25–2.5 | 0.50–2.0 | 1.50 |
| Part B | | | |
| Lanolin Oil | 5.0–15.0 | 8.0–12.0 | 10.60 |
| Cetyl Alcohol | 1.0–8.0 | 2.0–7.0 | 4.20 |
| Stearyl Alcohol | 0.50–6.0 | 0.75–5.0 | 1.50 |
| Cod Liver Oil | 1.0–7.0 | 1.0–4.0 | 2.00 |
| Butylated Hydroxytoluene | 0.10–1.0 | 0.20–0.80 | 0.50 |
| Part C | | | |
| Methylparaben | 0.10–0.50 | 0.15–0.40 | 0.30 |
| Propylparaben | 0.10–0.50 | 0.15–0.40 | 0.25 |
| Diazolidinyl Urea | 0.05–0.25 | 0.10–0.20 | 0.15 |
| Allantoin | 0.50–2.0 | 1.0–2.0 | 1.50 |
| Fragrance | 0.05–0.50 | 0.10–0.40 | 0.20 |
| Part D | | | |
| Triethanolamine (99%) | 0.05–3.0 | 0.20–2.0 | 0.80 |

Example 9

Preparation of Allantoin-Containing Skin Cream with Galactoarabinan, Sodium Lauryl Sulfate, and Beeswax An allantoin-containing skin cream with galactoarabinan, sodium lauryl sulfate, and beeswax is prepared according to Table 11. The preparation follows the method used in Example 3. The citric acid is used to adjust the pH.

TABLE 11

ALLANTOIN-CONTAINING SKIN CREAM WITH GALACTOARABINAN, SODIUM LAURYL SULFATE, AND BEESWAX

| INGREDIENT | RANGE | PREFERRED | OPTIMUM |
|---|---|---|---|
| Part A | | | |
| Water | 50.0–90.0 | 60.0–80.0 | 61.65 |
| Propylene Glycol | 2.0–9.0 | 4.0–7.0 | 5.70 |
| Sodium Lauryl Sulfate (30%) | 0.50–5.0 | 1.0–3.0 | 1.90 |
| Tetrasodium EDTA | 0.05–0.30 | 0.10–0.20 | 0.15 |
| Galactoarabinan | 1.0–25.0 | 3.0–15.0 | 5.00 |
| Citric Acid | 0.05–0.25 | 0.10–0.20 | 0.15 |
| Part B | | | |
| Lanolin Oil | 5.0–15.0 | 8.0–12.0 | 10.60 |
| Cetyl Alcohol | 1.0–8.0 | 2.0–7.0 | 4.20 |
| Stearyl Alcohol | 0.50–6.0 | 1.0–4.0 | 2.00 |
| Beeswax | 0.50–5.0 | 1.0–3.0 | 1.90 |
| Cod Liver Oil | 0.50–15.0 | 1.0–10.0 | 2.00 |
| Butylated Hydroxytoluene | 0.10–3.0 | 0.25–2.5 | 0.50 |

TABLE 11-continued

ALLANTOIN-CONTAINING SKIN CREAM WITH GALACTOARABINAN, SODIUM LAURYL SULFATE, AND BEESWAX

| INGREDIENT | RANGE | PREFERRED | OPTIMUM |
|---|---|---|---|
| Part C | | | |
| Methylparaben | 0.10–0.50 | 0.15–0.40 | 0.30 |
| Propylparaben | 0.10–0.50 | 0.15–0.40 | 0.25 |
| Allantoin | 0.50–2.0 | 1.0–2.0 | 1.50 |
| Fragrance | 0.05–0.50 | 0.10–0.40 | 0.20 |

Example 10

Treatment of Epidermolysis Bullosa with Allantoin-Containing Skin Cream

A female epidermolysis bullosa patient (A.B.) was treated with the allantoin-containing skin cream of Example 2 prepared in accordance with the optimum formulation recited in Table 3. The allantoin-containing skin cream used for treatment comprised 68.68% water, 1.90% 30% sodium lauryl sulfate solution, 0.15% tetrasodium EDTA, 0.12% citric acid, 10.60% lanolin oil, 4.20% cetyl alcohol, 2.00% stearyl alcohol, 1.90% beeswax, 2.00% cod liver oil, 0.50% butylated hydroxytoluene, 0.10% St. John's wort, 0.10% chamomile extract, 0.10% witch hazel extract, 0.10% arnica extract, 0.30% methylparaben, 0.20% propylparaben, 1.50% allantoin, and 0.20% fragrance. The patient A.B. was born with recessive dystrophic epidermolysis bullosa. She was born with no skin on her right foot from the shin down and spent the first 32 days of her life in intensive care. Her skin, which was constantly covered with Aquaphor, had the strength of tissue paper and blistered from the slightest touch. Although her feet, legs, arms, and hands were bandaged constantly, they continued to blister beneath the bandages. Her daily dressing changes took over an hour, and she required pain medication prior to each dressing change. Regardless of the meticulous care that the patient received, she battled infection constantly and chronic areas refused to heal. She began to develop infections that her doctors were unable to treat with antibiotics. Since her birth, the patient had required several different topical and oral antibiotics, as well as intramuscular injections. Because of the poor condition of her feet, the occupational and physical therapists treating the patient seriously doubted that she would ever walk.

The skin cream of Example 2 began to be applied to the patient A.B. when she was approximately 9½ months old. The registered nurses that cared for the patient A.B. at her home immediately observed that the cream cut the healing time for an open wound in half and actually kept blisters from spreading over larger areas. As absolutely no irritation was observed and tremendous improvement was seen for the areas receiving the cream, the cream then was applied to all unbandaged areas of the body of the patient 5 to 6 times daily. A remarkable reduction in the number of blisters was noticed, and the purplish colors of the scars began to fade. After continued success with the skin cream of Example 2, it began to be used on the patient under the bandaged areas in place of the Aquaphor.

For approximately four months, the cream was applied to both the bandaged and the unbandaged areas of the patient A.B. For the first time since her birth, her right foot completely healed and was without any open sore or blister.

The registered nurses that cared for the patient in her home continued to note a remarkable reduction in the amount of blistering, both under the bandages and on the open skin. The healing time for newly blistered areas was much faster. The areas healed without the milia cysts that, prior to using the cream, accompanied each scar.

No type of antibiotic has been applied to the patient since the cream started to be used on the patient. Despite the lack of use of antibiotic, her foot remained infection free. The period during which the cream of Example 2 was used was the longest period for which her foot had gone without reblistering and/or becoming infected.

At the last visit of the doctors to the patient, the doctors were amazed to see skin on areas of the foot that they never thought would heal. The patient is able to walk better and for longer areas of time, and she was able to actually run across the floor.

The patient had experienced an overall decrease in skin fragility. Her right lower extremity, the area of greatest blistering, has continued to have decreased erythema, decreased pain, and decreased skin fragility. The patient did not require any bacterial cultures or antibiotics over the period during which the skin cream of Example 2 was used.

Dressing changes were accomplished in half the time and without any pain medication. The mother of the patient was able to actually change her dressings alone. Before the cream of Example 2 was applied to the patient, this task was impossible for the mother of the patient because of the poor condition of her feet and the additional steps and time necessary to change the dressings prior to the use of the cream of Example 2 on the patient.

One area of the patient did not receive the cream: the buttocks area. At one point, the patient developed two very small blisters in that area about the size of a dime. One of the blisters continued to spread and spread until the blister covered the entire buttocks area. The area was raw and the blister continued to refill. No area on her body had had blisters spread since the cream of Example 2 had been used on the patient. This is the only area in which the cream was not used because no blisters had developed in that area prior to this. This strongly suggests that the cream was responsible for making a remarkable difference in the healing and protection of the skin of the patient.

Although the patient, as with all patients with recessive dystrophic epidermolysis bullosa, continued to have areas of scarring on hands with concern of eventual fusion and decreased function, her disease had stabilized after the use of the cream of Example 2.

Figure 1B:
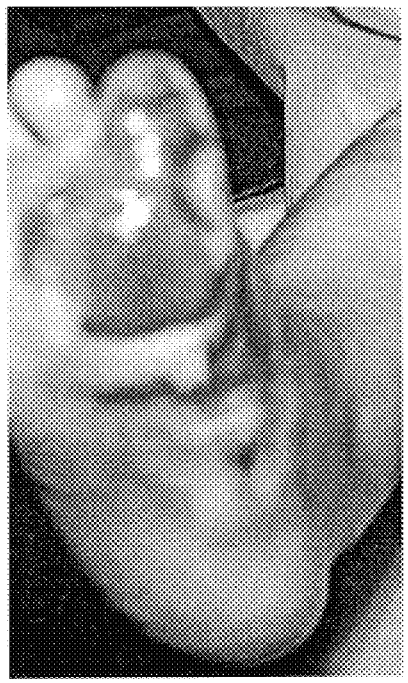

FIGS. 1(a) and 1(b) are pictures of the right foot of the patient A.B. before the use of the cream of Example 2 from two different views, showing the severity of the disease.

Figure 2:
FIG. 2 is a picture of the right foot of the patient A.B. after two months of use of the cream of Example 2, showing considerable improvement.

FIG. 2 is a picture of the right foot of the patient A.B. after two months of use of the cream of Example 2, showing considerable improvement.

Figure 3A:
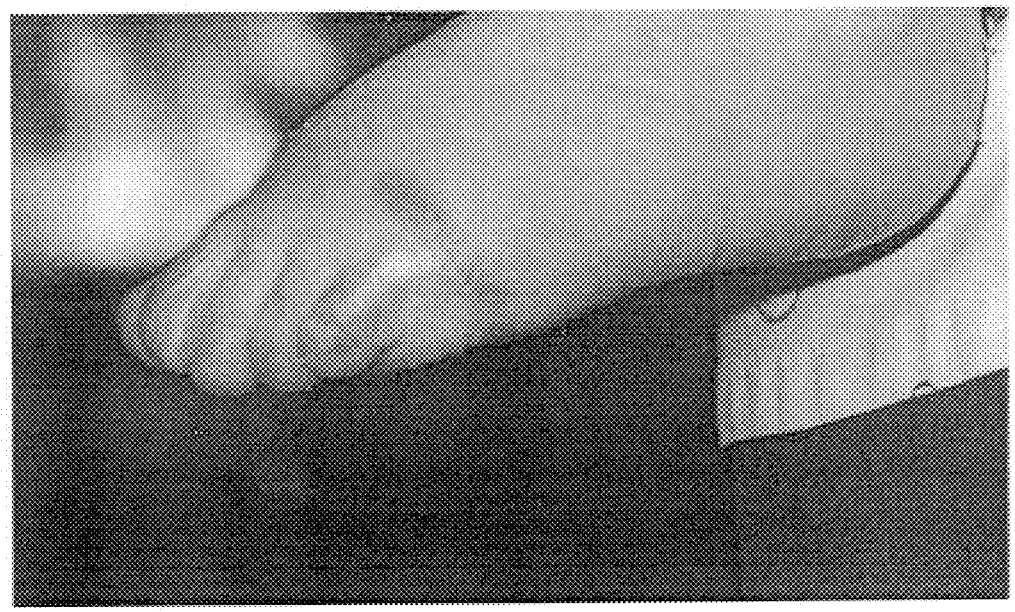
FIGS. 3(a) and 3(b) are pictures of the right foot of the patient A.B. after 12 months of use of the cream of Example 2, showing substantial improvement and clearing of the lesions.
Figure 3B:

FIGS. 3(a) and 3(b) are pictures of the right foot of the patient A.B. after 12 months of use of the cream of Example 2, showing substantial improvement and clearing of the lesions.

Figure 4A:
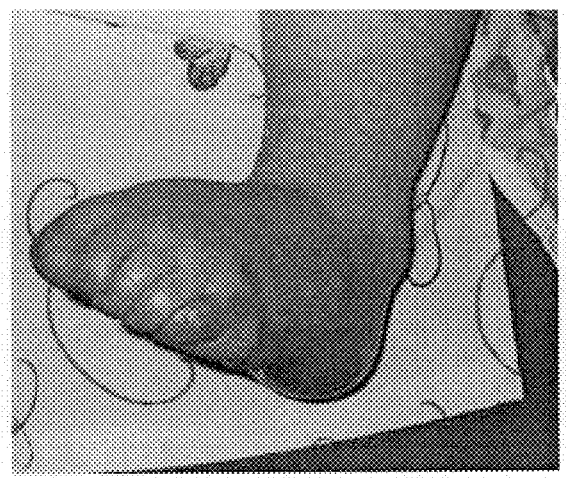
FIGS. 4(a), 4(b), and 4(c) are additional pictures of the right foot of the patient A.B. after 12 months of use of the cream of Example 2, again showing substantial improvement and clearing of the lesions.
Figure 4B:
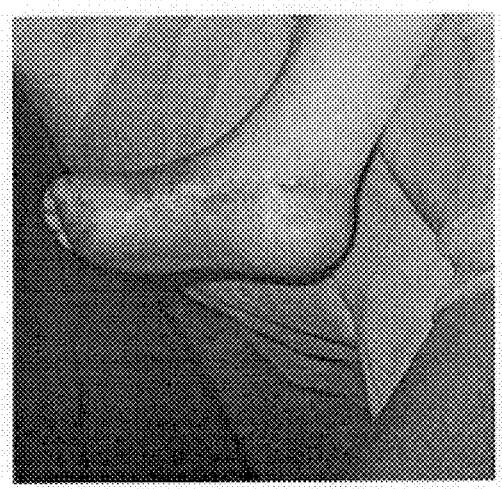
Figure 4C:

FIGS. 4(a), 4(b), and 4(c) are additional pictures of the right foot of the patient A.B. after 12 months of use of the cream of Example 2, again showing substantial improvement and clearing of the lesions.

Figure 5A:
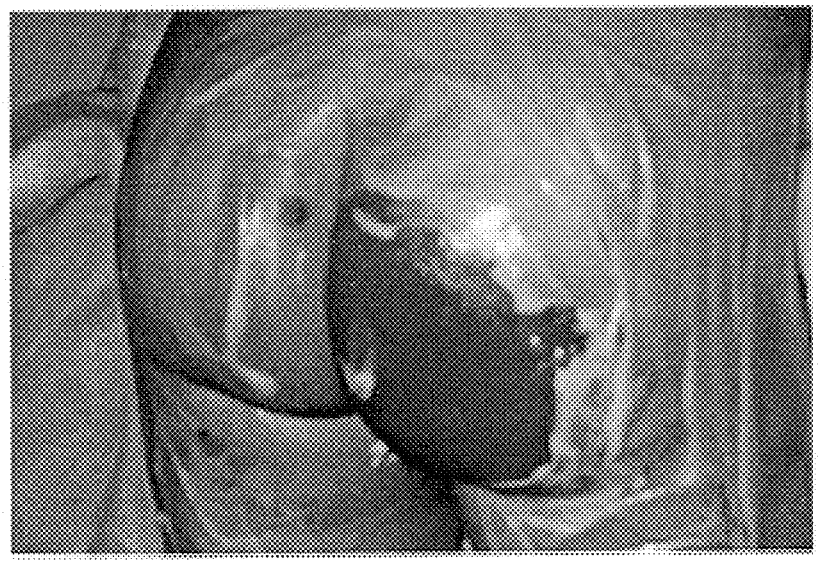
FIGS. 5(a) and 5(b) are pictures of the buttocks area of the patient A.B. before the use of the cream (FIG. 5(a)) and after 2 weeks of use of the cream of Example 2 (FIG. 5(b)), showing substantial improvement and clearing of the lesions.
Figure 5B:
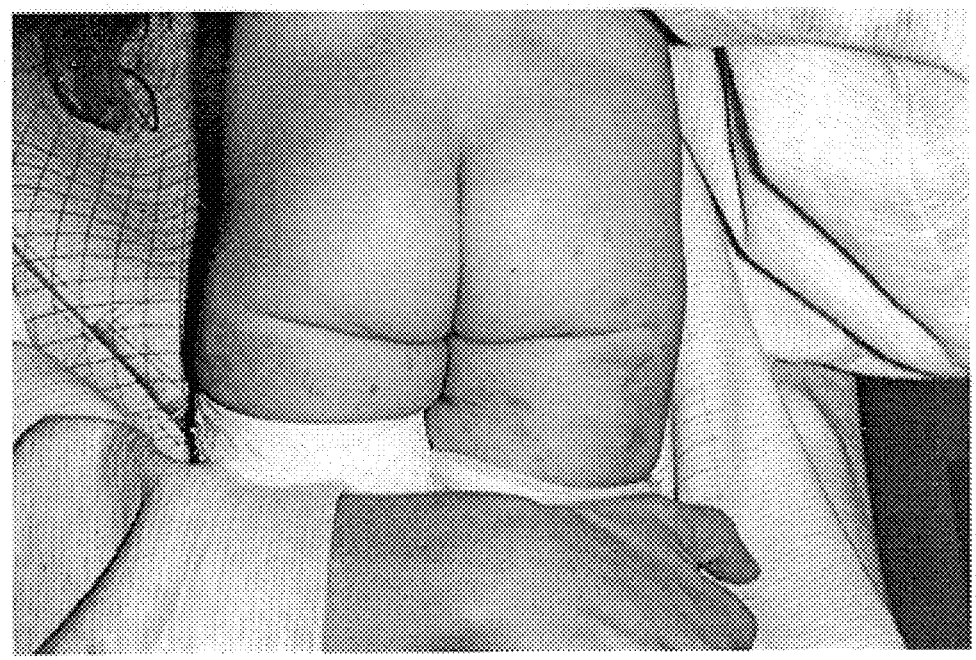

FIGS. 5(a) and 5(b) are pictures of the buttocks area of the patient A.B. before the use of the cream (FIG. 5(a)) and after 2 weeks of use of the cream (FIG. 5(b)), showing substantial improvement and clearing of the lesions.

Figure 6A:
FIGS. 6(a) and 6(b) are pictures of the facial area of the patient A.B. before the use of the cream (FIG. 6(a)) and after 3 months of use of the cream of Example 2 (FIG. 6(b)), showing substantial improvement, fading, and clearing of the lesions.
Figure 6B:
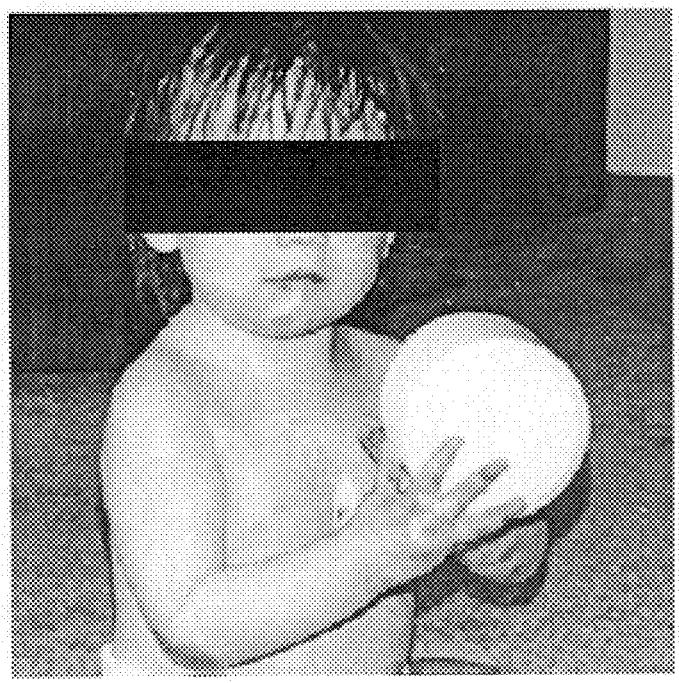

FIGS. 6(a) and 6(b) are pictures of the facial area of the patient A.B. before the use of the cream (FIG. 6(a)) and after 3 months of use of the cream (FIG. 6(b)), showing substantial improvement, fading, and clearing of the lesions.

Example 11

Treatment of Epidermolysis Bullosa

A female epidermolysis bullosa patient (C.D.) was treated with the allantoin-containing skin cream of Example 2. The patient C.D. had epidermolysis bullosa of the Dowling-Meara type.

The patient C.D. received two to three applications per day of the allantoin-containing skin cream of Example 2. The cream produced considerable improvement in the skin of the patient C.D. This was the first time that her skin had remained moderately clear for a long period of time. The areas that experienced severe blistering had remained clean with the exception of some minor blistering. This blistering was not nearly as severe as what had been experienced prior to the use of the skin cream of Example 2. Also, a blister that did start on the back of the patient C.D. did not develop into a full-blown, spread-wide blister as had happened previously. This tendency of these blisters to spread is characteristic of the Dowling-Meara form of epidermolysis bullosa. Even problem areas that have taken a longer time to heal have not spread out of control.

The time required for the care of the patient C.D., such as the time required for lancing and wrapping her wounds, has decreased by at least 75% subsequent to the administration of the allantoin-containing skin cream of Example 2. The requirements for medical supplies used for the care of the patient C.D., such as sterile needles, sterile bandages, and sterile dressing sponges, also decreased tremendously subsequent to the administration of the allantoin-containing skin cream of Example 2.

Figure 7:
FIG. 7 is a photograph of a second patient (C.D.) before commencement of the use of the allantoin-containing skin cream of Example 2.

FIG. 7 is a photograph of patient C.D. before commencement of the use of the allantoin-containing skin cream of Example 2.

Figure 8:
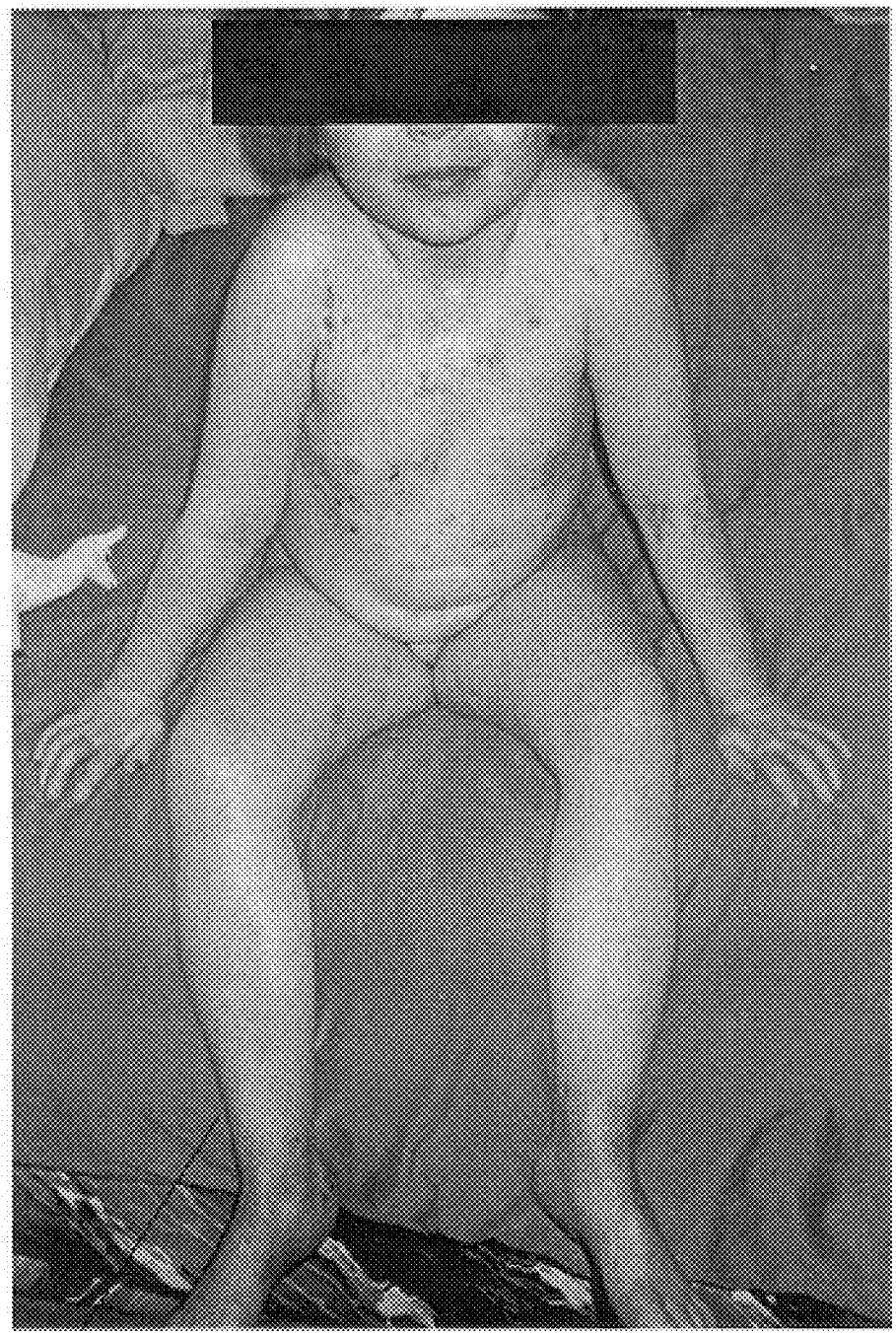
FIG. 8 is a photograph of patient C.D. after 8 weeks of use of the allantoin-containing skin cream of Example 2, showing substantial improvement of the lesions.

FIG. 8 is a photograph of patient C.D. after 8 weeks of use of the allantoin-containing skin cream of Example 2, showing substantial improvement of the lesions.

Figure 9A:
FIG. 9(a) is a photograph of the back area of patient C.D. before commencement of the use of the allantoin-containing skin cream of Example 2.

FIG. 9(a) is a photograph of the back area of patient C.D. before commencement of the use of the allantoin-containing skin cream of Example 2.

Figure 9B:
FIG. 9(b) is another photograph of the back area of patient C.D. before commencement of the use of the allantoin-containing skin cream of Example 2.

FIG. 9(b) is another photograph of the back area of patient C.D. before commencement of the use of the allantoin-containing skin cream of Example 2.

Figure 10A:
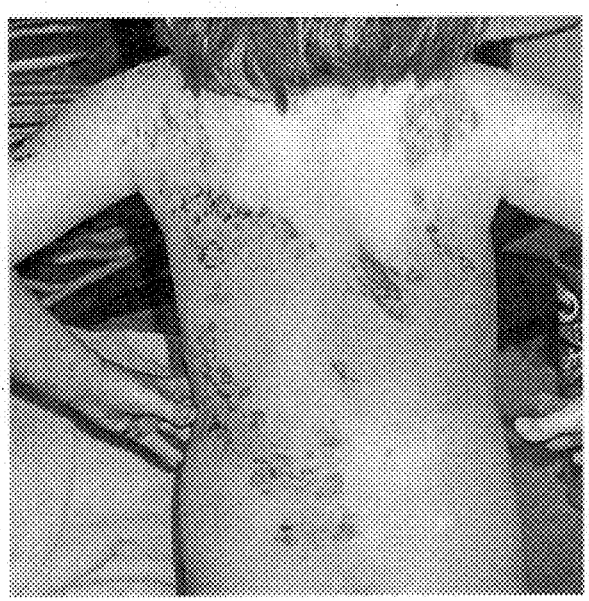
FIG. 10(a) is a photograph of the upper back area of patient C.D. after 2 weeks of use of the allantoin-containing skin cream of Example 2, showing considerable improvement.

FIG. 10(a) is a photograph of the upper back area of patient C.D. after 2 weeks of use of the allantoin-containing skin cream of Example 2, showing considerable improvement.

Figure 10B:
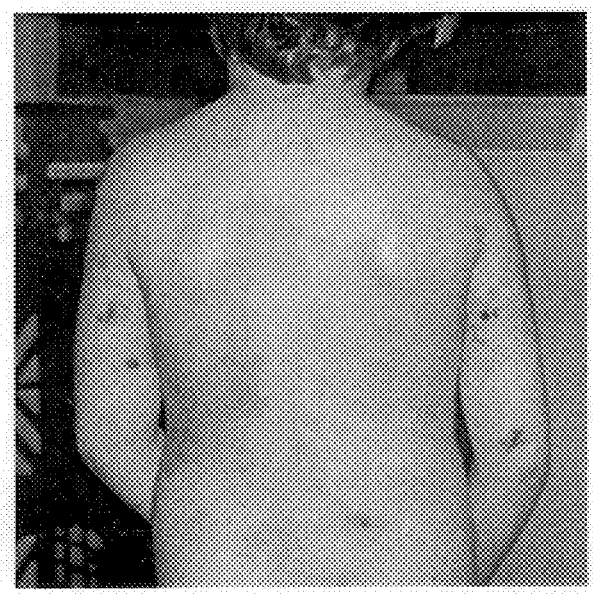
FIG. 10(b) is a photograph of the upper back area of patient C.D. after 8 weeks of use of the allantoin-containing skin cream of Example 2, showing continued improvement evidenced by fading of the lesions.

FIG. 10((b) is a photograph of the upper back area of patient C.D. after 8 weeks of use of the allantoin-containing skin cream of Example 2, showing continued improvement evidenced by fading of the lesions.

Figure 11A:
FIG. 11(a) is a photograph of the upper leg area of patient C.D. before commencement of the use of the allantoin-containing skin cream of Example 2.

FIG. 11(a) is a photograph of the upper leg area of patient C.D. before commencement of the use of the allantoin-containing skin cream of Example 2.

Figure 11B:
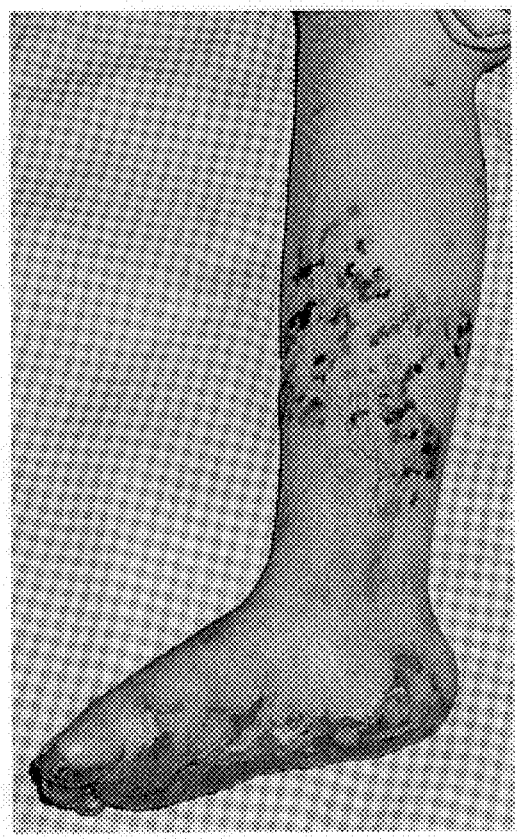
FIG. 11(b) is a photograph of the lower leg area of patient C.D. before commencement of the use of the allantoin-containing skin cream of Example 2.

FIG. 11(b) is a photograph of the lower leg area of patient C.D. before commencement of the use of the allantoin-containing skin cream of Example 2.

Figure 11C:
FIG. 11(c) is a photograph of the legs of patient C.D. after 2 weeks of use of the allantoin-containing skin cream of Example 2, showing substantial improvement.

FIG. 11(c) is a photograph of the legs of patient C.D. after 2 weeks of use of the allantoin-containing skin cream of Example 2, showing substantial improvement.

Figure 11D:
FIG. 11(d) is a photograph of the legs of patient C.D. after 8 weeks of use of the allantoin-containing skin cream of Example 2, showing continuing improvement.

FIG. 11(d) is a photograph of the legs of patient C.D. after 8 weeks of use of the allantoin-containing skin cream of Example 2, showing continuing improvement.

Advantages of the Present Invention

The present invention provides an improved method of treating skin diseases and conditions characterized by ulceration, inflammation, and blistering. This includes such difficult-to-treat conditions as epidermolysis bullosa, decubitus ulcers, diabetic ulcers, pressure ulcers, and milia. Methods according to the present invention provide rapid improvement, are well tolerated by patients, are easy to apply, and can be used alone or with other methods for treatment of skin conditions.

Although the present invention has been described in considerable detail, with reference to certain preferred versions thereof, other versions and embodiments are possible. Therefore, the scope of the invention is determined by the following claims.

I claim:

1. A method of treating epidermolysis bullosa comprising applying to the skin of patients in need thereof an allantoin-containing composition comprising an oil-in-water emulsion comprising:
   (a) allantoin;
   (b) an emulsifier system including:
      (i) beeswax; and
      (ii) an anionic emulsifier that is substantially hydrophilic and is soluble in water, the pH of the composition being from about 3.0 to about 6.0 after the addition of an acid,
   wherein the allantoin is stable in the emulsion across the pH range from about 3.0 to about 6.0.

2. The method of claim 1 wherein the pH of the composition is from about 4.5 to about 5.8.

3. The method of claim 1 wherein the emulsifier is selected from the group consisting of ammonium lauryl sulfate, sodium lauryl sulfate, sodium laureth sulfate, sodium oleyl succinate, ammonium lauryl sulfosuccinate, sodium dodecylbenzenesulfonate, ammonium laureth sulfate, and sodium lauryl sarcosinate.

4. The method of claim 3 wherein the emulsifier is sodium lauryl sulfate.

5. The method of claim 1 further comprising administering an additional therapeutic agent in a therapeutically effective quantity.

6. The method of claim 5 wherein the additional therapeutic agent is selected from the group consisting of steroids, nonsteroidal anti-inflammatory agents, leukotriene antagonists, and monoclonal antibodies.

7. The method of claim 1 wherein the composition further comprises at least one of:
   (a) an emollient component comprising at least one ingredient selected from the group consisting of lanolin oil, cetyl alcohol, stearyl alcohol, and cod liver oil;
   (b) butylated hydroxytoluene;
   (c) at least one herbal extract selected from the group consisting of St. John's wort extract, witch hazel extract, chamomile extract, and arnica extract;
   (d) a preservative component comprising at least one preservative selected from the group consisting of methylparaben and propylparaben;
   (e) tetrasodium EDTA; and
   (f) a solvent component comprising at least one solvent selected from the group consisting of propylene glycol, butylene glycol, and glycerin.

8. The method of claim 2 wherein the composition comprises:
   an oil-in-water emulsion comprising:
      (a) water;
      (b) sodium lauryl sulfate;
      (c) propylene glycol;
      (d) tetrasodium EDTA;
      (e) citric acid;
      (f) lanolin oil;
      (g) cetyl alcohol;
      (h) stearyl alcohol;
      (i) beeswax;
      (j) cod liver oil;
      (k) butylated hydroxytoluene;
      (l) St. John's wort extract;
      (m) witch hazel extract;
      (n) chamomile extract;
      (o) arnica extract;
      (p) methylparaben;
      (q) propylparaben;
      (r) allantoin; and
      (s) fragrance.

9. The method of claim 8 wherein the composition comprises:
   (a) from about 50% to about 90% of water;
   (b) from about 0.5% to about 2.5% of 30% sodium lauryl sulfate;
   (c) from about 2.0% to about 9.0% of propylene glycol;
   (d) from about 0.05% to about 0.5% of tetrasodium EDTA;
   (e) from about 0.05% to about 0.5% of citric acid;
   (f) from about 5% to about 15% of lanolin oil;
   (g) from about 3% to about 10% of cetyl alcohol;
   (h) from about 1% to about 5% of stearyl alcohol;
   (i) from about 0.5% to about 2.5% of beeswax;
   (j) from about 1.0% to about 7.0% of cod liver oil;
   (k) from about 0.1% to about 1.0% of butylated hydroxytoluene;
   (l) from about 0.05% to about 0.5% of St. John's wort extract;
   (m) from about 0.05% to about 0.5% of witch hazel extract;
   (n) from about 0.05% to about 0.5% of chamomile extract;
   (o) from about 0.05% to about 0.5% of arnica extract;
   (p) from about 0.1% to about 0.5% of methylparaben;
   (q) from about 0.1% to about 0.5% of propylparaben;
   (r) from about 0.5% to about 2% of allantoin; and
   (s) from about 0.05% to about 0.5% of fragrance.

10. The method of claim 9 wherein the composition comprises:
   (a) from about 55% to about 75% of water;
   (b) from about 1.0% to about 2.5% of 30% sodium lauryl sulfate;
   (c) from about 3.0% to about 6.0% of propylene glycol;
   (d) from about 0.1% to about 0.3% of tetrasodium EDTA;
   (e) from about 0.08 to about 0.35% of citric acid;
   (f) from about 8.0% to about 12.0% of lanolin oil;
   (g) from about 3.5% to about 7.5% of cetyl alcohol;
   (h) from about 1.0% to about 3.0% of stearyl alcohol;
   (i) from about 1.0% to about 2.5% of beeswax;
   (j) from about 1.0% to about 4.0% of cod liver oil;

(k) from about 0.2% to about 0.8% of butylated hydroxytoluene;
(l) from about 0.05% to about 0.15% of St. John's wort extract;
(m) from about 0.05% to about 0.15% of witch hazel extract;
(n) from about 0.05% to about 0.15% of chamomile extract;
(o) from about 0.05% to about 0.15% of arnica extract;
(p) from about 0.15% to about 0.40% of methylparaben;
(q) from about 0.10% to about 0.30% of propylparaben;
(r) from about 0.50% to about 2.0% of allantoin; and
(s) from about 0.1% to about 0.3% of fragrance.

11. The method of claim 10 wherein the composition comprises:

(a) about 68.68% of water;
(b) about 1.9% of sodium lauryl sulfate;
(c) about 5.3% of propylene glycol;
(d) about 0.15% of tetrasodium EDTA;
(e) about 0.12% of citric acid;
(f) about 10.6% of lanolin oil;
(g) about 4.2% of cetyl alcohol;
(h) about 2.0% of stearyl alcohol;
(i) about 1.90% of beeswax;
(j) about 2.0% of cod liver oil;
(k) about 0.5% of butylated hydroxytoluene;
(l) about 0.1% of St. John's wort extract;
(m) about 0.1% of witch hazel extract;
(n) about 0.1% of chamomile extract;
(o) about 0.1% of arnica extract;
(p) about 0.3% of methylparaben;
(q) about 0.25% of propylparaben;
(r) about 1.50% of allantoin; and
(s) about 0.20% of fragrance.

* * * * *